(12) United States Patent
Jiang et al.

(10) Patent No.: US 11,464,984 B2
(45) Date of Patent: Oct. 11, 2022

(54) LEADLESS PACEMAKER SYSTEMS, DEVICES AND METHODS THAT MONITOR FOR ATRIAL CAPTURE

(71) Applicant: Pacesetter, Inc., Sylmar, CA (US)

(72) Inventors: Chunlan Jiang, Northridge, CA (US); Gene A. Bornzin, Santa Monica, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 17/141,093

(22) Filed: Jan. 4, 2021

(65) Prior Publication Data

US 2021/0236827 A1  Aug. 5, 2021

Related U.S. Application Data

(60) Provisional application No. 62/969,780, filed on Feb. 4, 2020.

(51) Int. Cl.
*A61N 1/37* (2006.01)
*A61N 1/375* (2006.01)
(Continued)

(52) U.S. Cl.
CPC ....... *A61N 1/3714* (2013.01); *A61N 1/36535* (2013.01); *A61N 1/37258* (2013.01);
(Continued)

(58) Field of Classification Search
CPC .. A61N 1/3714; A61N 1/37512; A61N 1/365; A61N 1/36535; A61B 5/353
See application file for complete search history.

(56) References Cited

U.S. PATENT DOCUMENTS 5,331,966 A    7/1994  Bennett et al.
6,101,416 A *  8/2000  Sloman ............... A61N 1/3712
                                                   607/9
(Continued)

FOREIGN PATENT DOCUMENTS

EP    1549213 B1    8/2007
EP    2364107 B1    9/2016

OTHER PUBLICATIONS

Extended European Search Report dated Jul. 7, 2021, European Patent Application No. 21151348.6-1122.

*Primary Examiner* — William J Levicky
(74) *Attorney, Agent, or Firm* — Vierra Magen Marcus LLP

(57) ABSTRACT

Systems, devices, and methods for monitoring for atrial capture are disclosed. Such a method, for use within an implantable system including an atrial leadless pacemaker (aLP) and a ventricular leadless pacemaker (vLP), includes storing within a memory of the vLP a paced atrial activation morphology template corresponding to far-field atrial signal components expected to be present in a vEGM sensed by the vLP when an atrial pacing pulse delivered by the aLP captures atrial tissue. The vLP senses a vEGM and compares a morphology of a portion of the sensed vEGM to the paced atrial activation morphology template to determine whether a match therebetween is detected. Additionally, the vLP determines whether atrial capture occurred or failed to occur (responsive to an atrial pacing pulse), based on whether the vLP detects a match between the morphology of a portion of the sensed vEGM and the paced atrial activation morphology template.

20 Claims, 11 Drawing Sheets

(51) Int. Cl.
*A61N 1/365* (2006.01)
*A61N 1/372* (2006.01)
*A61N 1/39* (2006.01)

(52) U.S. Cl.
CPC ..... *A61N 1/37264* (2013.01); *A61N 1/37512* (2017.08); *A61N 1/39622* (2017.08)

(56) References Cited

U.S. PATENT DOCUMENTS

| | | | |
|---|---|---|---|
| 6,650,931 B1 | 11/2003 | McClure et al. | |
| 6,912,418 B1 | 6/2005 | Florio | |
| 7,567,835 B2 | 7/2009 | Gunderson et al. | |
| 8,131,361 B2 | 3/2012 | Gill et al. | |
| 8,386,024 B2 | 2/2013 | Gunderson et al. | |
| 8,774,909 B2 | 7/2014 | Patel | |
| 8,781,585 B2 | 7/2014 | Gunderson et al. | |
| 8,792,971 B2 | 7/2014 | Gunderson et al. | |
| 9,278,218 B2 | 3/2016 | Karst et al. | |
| 9,375,580 B2 | 6/2016 | Bonner et al. | |
| 9,492,669 B2 | 11/2016 | Demmer et al. | |
| 9,522,283 B2 | 12/2016 | Bardy et al. | |
| 9,694,186 B2 | 7/2017 | Carney et al. | |
| 9,889,303 B2 | 2/2018 | Brown et al. | |
| 9,993,653 B2 | 6/2018 | Bardy et al. | |
| 10,342,981 B2 | 7/2019 | Ghosh et al. | |
| 2009/0099618 A1* | 4/2009 | Rousso | A61N 1/3702 607/17 |
| 2010/0121394 A1 | 5/2010 | Gill et al. | |
| 2013/0325081 A1 | 12/2013 | Karst et al. | |
| 2016/0023013 A1 | 1/2016 | Greenhut et al. | |
| 2016/0114169 A1* | 4/2016 | Sheldon | A61N 1/365 607/17 |
| 2018/0008831 A1* | 1/2018 | An | A61N 1/3756 |
| 2018/0185660 A1* | 7/2018 | Eddy | A61N 1/37512 |
| 2018/0214703 A1* | 8/2018 | Chin | A61N 1/3756 |
| 2019/0111270 A1 | 4/2019 | Zhou | |
| 2019/0336026 A1 | 11/2019 | Dawoud et al. | |

\* cited by examiner

LEADLESS PACEMAKER SYSTEMS, DEVICES AND METHODS THAT MONITOR FOR ATRIAL CAPTURE

PRIORITY CLAIM

This application claims priority to U.S. Provisional Patent Application No. 62/969,780, filed Feb. 4, 2020, which is incorporated herein by reference.

FIELD OF TECHNOLOGY

Embodiments described herein generally relate to systems, devices, and methods that can be used to monitor for atrial capture that is responsive to an atrial pacing pulse delivered by an atrial leadless pacemaker.

BACKGROUND

An implantable medical system can include both an atrial leadless pacemaker (aLP) configured to sense and pace in the right atrium (RA), and a ventricular leadless pacemaker (vLP) configured to sense and pace in the right ventricle (RV). Confirmation of pacing capture is important when performing cardiac pacing to ensure safety and atrial-ventricular (AV) synchronization. For example, when performing DDD pacing, the vLP should pace the RV at a specified AV delay following when the aLP paced the RA.

SUMMARY

Certain embodiments of the present technology, which are for use within an implantable system including an atrial leadless pacemaker (aLP) and a ventricular leadless pacemaker (vLP), are directed to a method for monitoring for atrial capture. Such a method includes storing within a memory of the vLP one or more morphology templates including a paced atrial activation morphology template corresponding to far-field atrial signal components expected to be present in a ventricular electrogram (vEGM) sensed by the vLP when an atrial pacing pulse delivered by the aLP captures atrial tissue. Additionally, the method includes the vLP sensing a vEGM using at least two electrodes of the vLP, and the vLP comparing a morphology of a portion of the sensed vEGM to the paced atrial activation morphology template to thereby determine whether a match therebetween is detected. The method also includes the vLP determining whether atrial capture occurred or failed to occur responsive to an atrial pacing pulse delivered by the aLP, based on whether the vLP detects a match between the morphology of a portion of the sensed vEGM and the paced atrial activation morphology template.

In accordance with certain embodiments, the morphology template(s) stored in the memory of the vLP includes at least first and second paced atrial activation morphology templates, wherein the first atrial activation morphology template corresponds to far-field atrial signal components expected to be present in a vEGM sensed by the vLP when an atrial pacing pulse delivered by the aLP captures atrial tissue and the patient has a first posture, and the second atrial activation morphology template corresponds to far-field atrial signal components expected to be present in a vEGM sensed by the vLP when an atrial pacing pulse delivered by the aLP captures atrial tissue and the patient has a second posture. In such an embodiment, the method further comprises: the vLP monitoring a posture of the patient using a sensor of the vLP, and selecting, based on the posture of the patient, one of the first and second paced atrial activation morphology templates to compare to a portion of the sensed vEGM to thereby determine whether a match therebetween is detected.

More generally, in accordance with certain embodiments, for one or more different type of morphology template stored in the memory of the vLP there are at least first and second versions of the morphology template, wherein the first version is to be used when the patient has a first posture, and the second version is to be used when the patient has a second posture, and the method further comprises monitoring a posture of the patient and selecting which version of the morphology templates are to be compared to the morphology of a portion of the sensed vEGM to thereby determine whether a match therebetween is detected.

In accordance with certain embodiments, the morphology template(s) stored in the memory of the vLP also includes an intrinsic atrial activation morphology template corresponding to far-field atrial signal components expected to be present in a vEGM sensed by the vLP when an intrinsic atrial activation occurs. The method can further comprise the vLP also comparing the morphology of a same portion of the sensed vEGM, that is compared to the paced atrial activation morphology template, to the intrinsic atrial activation morphology template to determine whether a match therebetween is detected. In such an embodiment, the vLP determining whether atrial capture occurred or failed to occur responsive to an atrial pacing pulse delivered by the aLP, is also based on whether the vLP detects a match between the morphology of the portion of the sensed vEGM and the intrinsic atrial activation morphology template.

In accordance with certain embodiments, the morphology template(s) stored in the memory of the vLP also includes an atrial pacing artifact morphology template corresponding to far-field atrial signal components expected to be present in a vEGM sensed by the vLP when an atrial pacing pulse is delivered by the aLP. In such an embodiment, the method can also include the vLP comparing a morphology of a portion of the sensed vEGM to the atrial pacing artifact morphology template to thereby determine whether a match therebetween is detected, and the vLP detecting an atrial pacing artifact when the vLP detects a match between the morphology of a portion of the sensed vEGM and the atrial pacing artifact morphology template. In certain embodiment, the vLP comparing the morphology of a portion of the sensed vEGM to the paced atrial activation morphology template to thereby determine whether a match therebetween is detected, is performed by the vLP in response to the vLP detecting a match between a morphology of a portion of the sensed vEGM and the atrial pacing artifact morphology template. Further, the portion of the sensed vEGM that the vLP compares to the paced atrial activation morphology template, in order to determine whether a match therebetween is detected, comprises a portion of the sensed vEGM within a specified window following where or when the atrial pacing artifact is detected.

In accordance with certain embodiments, the aLP and the vLP are configured to communicate with one another, and the aLP is configured to send an atrial pace notification message to the vLP prior to the aLP delivering an atrial pacing pulse to the atrium. The method also includes the vLP receiving the atrial pace notification message from the aLP. In such an embodiment, the vLP comparing the morphology of a portion of the sensed vEGM to the paced atrial activation morphology template to thereby determine whether a match therebetween is detected, is performed by the vLP in response to the vLP receiving the atrial pace notification message from the aLP. Additionally, the portion of the sensed vEGM that the vLP compares to the paced atrial activation morphology template, in order to determine whether a match therebetween is detected, comprises a portion of the sensed vEGM within a specified window following when or where the vLP receives the atrial pace notification message from the aLP.

In accordance with certain embodiments, where the aLP and the vLP are capable of communicating with one another by sending messages from one to the other, the aLP is configured to send an atrial pace notification message to the vLP prior to the aLP delivering an atrial pacing pulse to the atrium. The morphology template(s) stored in the memory of the vLP also includes an atrial pacing artifact morphology template corresponding to far-field atrial signal components expected to be present in a vEGM sensed by the vLP when an atrial pacing pulse is delivered by the aLP. In such an embodiment, the method can further comprise the vLP monitoring communication quality between the aLP and the vLP. When the communication quality is above a specified threshold, the vLP monitors for a said atrial pace notification message sent by the aLP, and the portion of the sensed vEGM that the vLP compares to the paced atrial activation morphology template, in order to determine whether a match therebetween is detected, comprises a portion of the sensed vEGM within a specified window following when or where the vLP receives a said atrial pace notification message from the aLP. When the communication quality is below the specified threshold, the vLP monitors for an atrial pacing artifact using the atrial pacing artifact morphology template, and the portion of the sensed vEGM that the vLP compares to the paced atrial activation morphology template, in order to determine whether a match therebetween is detected, comprises a portion of the sensed vEGM within a specified window following when or where the vLP detects an atrial pacing artifact.

The vLP monitoring the communication quality between the aLP and the vLP can comprise at least one of the following: the vLP performing error detection and correction on one or more messages received from the aLP and determining the communication quality based on results of the error detection and correction; the vLP measuring an amplitude or power of a received signal including one or more messages received from the aLP and determining the communication quality based on results of the measuring the amplitude or power; the vLP measuring noise associated with a channel over which messages are received from the aLP and determining the communication quality based on results of the measuring noise; or the vLP measuring time intervals between one or more consecutive messages received from the aLP and determining the communication quality based on the measured time intervals. In such an embodiment, the communication quality is indicative of at least one of a quality of one or more messages or a quality of the channel over which one or more messages are received by the vLP from the aLP.

In accordance with certain embodiments, after the vLP determines that atrial capture failed to occur responsive to an atrial pacing pulse delivered by the aLP, the vLP sends a message to the aLP to inform the aLP that atrial capture failed and/or to instruct the aLP to increase a voltage of one or more further atrial pacing pulses.

In accordance with certain embodiments, after the vLP determines that atrial capture occurred responsive to an atrial pacing pulse delivered by the aLP, the vLP sends a message to the aLP to inform the aLP that atrial capture succeeded and/or to instruct the aLP to decrease a voltage of one or more further atrial pacing pulses.

In accordance with certain embodiments, after a match is detected between a said morphology template stored in the memory of the vLP and a portion of the sensed vEGM, the portion of the sensed vEGM that matched the said morphology template is used to update the said morphology template stored in the memory.

Certain embodiments of the present technology are directed to an implantable system, comprising: an aLP and a vLP. The aLP includes a pulse generator configured to produce pacing pulses, and at least two electrodes electrically coupled to the pulse generator and configured to deliver pacing pulses produced by the pulse generator to a patient's atrium. The vLP includes at least two electrodes, a sensing circuit electrically coupled to the at least two electrodes of the vLP and configured to sense a vEGM, and a memory that stores one or more morphology templates. The stored morphology template(s) include a paced atrial activation morphology template corresponding to far-field atrial signal components expected to be present in the vEGM when an atrial pacing pulse delivered by the aLP captures atrial tissue. The vLP also includes at least one of a processor or controller configured to: compare a morphology of a portion of the sensed vEGM to the paced atrial activation morphology template to thereby determine whether a match therebetween is detected; determine that atrial capture occurred responsive to an atrial pacing pulse delivered by the aLP, based on a match being detected between the morphology of a portion of the sensed vEGM and the paced atrial activation morphology template; and determine that atrial capture failed to occur responsive to an atrial pacing pulse delivered by the aLP, based on a match failing to be detected between the morphology of a portion of the sensed vEGM and the paced atrial activation morphology template.

In accordance with certain embodiments, the morphology template(s) stored in the memory of the vLP also includes an intrinsic atrial activation morphology template corresponding to far-field atrial signal components expected to be present in a vEGM sensed by the vLP when an intrinsic atrial activation occurs. The at least one of a processor or controller of the vLP is configured to: compare the morphology of a same portion of the sensed vEGM, that is compared to the paced atrial activation morphology template, to the intrinsic atrial activation morphology template to determine whether a match therebetween is detected; and determine whether atrial capture occurred or failed to occur responsive to an atrial pacing pulse delivered by the aLP, also based on whether the vLP detects a match between the morphology of the portion of the sensed vEGM and the intrinsic atrial activation morphology template.

In accordance with certain embodiments, the morphology template(s) stored in the memory of the vLP also includes an atrial pacing artifact morphology template corresponding to far-field atrial signal components expected to be present in a vEGM sensed by the vLP when an atrial pacing pulse is delivered by the aLP. The at least one of a processor or controller of the vLP is configured to: compare a morphology of a portion of the sensed vEGM to the atrial pacing artifact morphology template to thereby determine whether a match therebetween is detected; and detect an atrial pacing artifact when the vLP detects a match between the morphology of a portion of the sensed vEGM and the atrial pacing artifact morphology template. Further, the portion of the sensed vEGM that is compared to the paced atrial activation morphology template, in order to determine whether a match therebetween is detected, comprises a portion of the sensed vEGM within a specified window following where or when the atrial pacing artifact is detected.

In accordance with certain embodiments, for one or more different types of morphology templates stored in the memory of the vLP there are at least first and second versions of the morphology template, wherein the first version is to be used when the patient has a first posture, and the second version is to be used when the patient has a second posture. Further, the vLP comprises a sensor that can be used to monitor a posture of a patient within which the vLP and the aLP is implanted. In such an embodiment, the at least one of a processor or controller of the vLP can be configured to monitor the posture of the patient using the sensor, and select, based on the monitored posture of the patient, which version of one or more of the morphology templates is/are to be compared to the morphology of a portion of the sensed vEGM to thereby determine whether a match therebetween is detected.

In accordance with certain embodiments, a leadless pacemaker (LP) comprises at least two electrodes, a sensing circuit electrically coupled to the at least two electrodes and configured to sense an electrogram (EGM), and a memory that stores one or more morphology templates including a first morphology template corresponding to far-field signal components expected to be present in the EGM when a pacing pulse delivered to a remote cardiac chamber by a further LP captures tissue of the remote cardiac chamber. The LP also includes at least one of a processor or controller configured to compare a morphology of a portion of the sensed EGM to the first template to thereby determine whether a match therebetween is detected; determine that capture of the remote cardiac chamber occurred responsive to a pacing pulse delivered by the further LP, based on a match being detected between the morphology of a portion of the sensed EGM and the first morphology template; and determine that capture of the remote cardiac chamber failed to occur responsive to a pacing pulse delivered by the further LP, based on a match failing to be detected between the morphology of a portion of the sensed EGM and the first morphology template.

In accordance with certain embodiments, the morphology template(s) stored in the memory of the LP also includes a second morphology template corresponding to far-field signal components expected to be present in an EGM sensed by the LP when an intrinsic activation of the remote chamber occurs. Further, the at least one of a processor or controller of the LP is configured to: compare the morphology of a same portion of the sensed EGM, that is compared to the first morphology template, to the second morphology template to determine whether a match therebetween is detected; and determine whether capture of the remote chamber occurred or failed to occur responsive to a pacing pulse delivered by the further LP, also based on whether the LP detects a match between the morphology of the portion of the sensed EGM and the second morphology template.

In accordance with certain embodiments, the morphology template(s) stored in the memory of the LP also includes a third morphology template corresponding to far-field signal components expected to be present in an EGM sensed by the LP when a pacing pulse is delivered by the further LP to the remote chamber. Further, the at least one of a processor or controller of the LP is configured to: compare a morphology of a portion of the sensed EGM to the third morphology template to thereby determine whether a match therebetween is detected; and detect a pacing artifact from the remote chamber when the LP detects a match between the morphology of a portion of the sensed vEGM and the third morphology template. Additionally, the portion of the sensed EGM that is compared to the first template, in order to determine whether a match therebetween is detected, comprises a portion of the sensed EGM within a specified window following where or when the atrial pacing artifact is detected.

In accordance with certain embodiments, the LP is configured to receive messages from the further LP. Further, the at least one of a processor or controller of the LP is configured to monitor communication quality between the further LP and the LP. When the communication quality is above a specified threshold, the LP monitors for a pace notification message sent by the further LP, and the portion of the sensed EGM that is compared to the first morphology template, in order to determine whether a match therebetween is detected, comprises a portion of the sensed EGM within a specified window following when or where the LP receives a pace notification message from the further LP. When the communication quality is below the specified threshold, the LP monitors for a pacing artifact using the second morphology template, and the portion of the sensed EGM that is compared to the first morphology template, in order to determine whether a match therebetween is detected, comprises a portion of the sensed EGM within a specified window following when or where the LP detects a pacing artifact.

In accordance with certain embodiments, for one or more different type of morphology template stored in the memory of the LP there are at least two versions of the morphology template. Further, the LP comprises a sensor that can be used to monitor a posture of a patient within which the LP and the further LP are implanted. The at least one of a processor or controller of the LP is configured to monitor a posture of the patient using the sensor, and select, based on the monitored posture of the patient, which version of one or more types of morphology templates stored in the memory is/are to be compared to the morphology of a portion of the sensed EGM to thereby determine whether a match therebetween is detected.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Certain embodiments of the present technology relate to implantable systems, and methods for use therewith, that can monitor for atrial capture.

Before providing addition details of the specific embodiments of the present technology mentioned above, an exemplary system in which embodiments of the present technology can be used will first be described with reference to FIGS. 1A, 1B and 2. More specifically, FIGS. 1A, 1B and 2 will be used to describe an exemplary cardiac pacing system, wherein pacing and sensing operations can be performed by multiple medical devices, which may include one or more leadless pacemakers (LPs), an implantable cardioverter-defibrillator (ICD), such as a subcutaneous-ICD, and/or a programmer reliably and safely coordinate pacing and/or sensing operations.

Figure 1A:
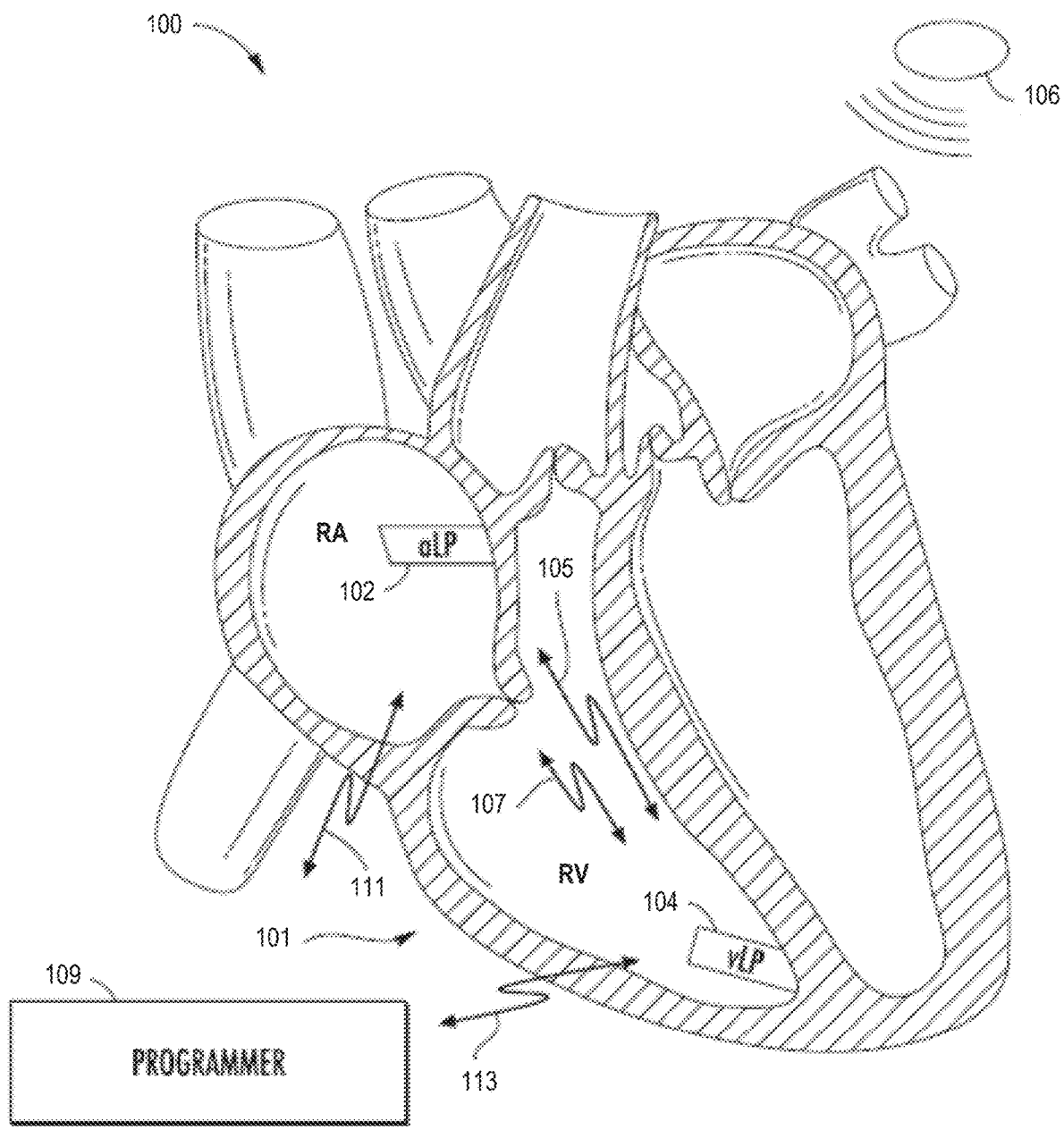
FIG. 1A illustrates a system formed in accordance with certain embodiments described herein as implanted in a heart.

FIG. 1A illustrates a system 100 formed in accordance with certain embodiments herein as implanted in a heart 101. The system 100 comprises two or more leadless pacemakers (LPs) 102 and 104 located in different chambers of the heart. LP 102 is located in a right atrium (RA), while LP 104 is located in a right ventricle (RV). The RA is also known as the right atrial chamber, and the RV is also known as the right ventricular chamber. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located. Since the LP 102 is located in an atrium, the LP 102 can also be referred to as an atrial LP (aLP). Similarly, since the LP 104 is located in a ventricle, the LP 104 can also be referred to as a ventricular LP (vLP).

In some embodiments, LPs 102 and 104 communicate with one another, with an ICD 106, and with an external device (programmer) 109 through wireless transceivers, communication coils and antenna, and/or by conductive communication through the same electrodes as used for sensing and/or delivery of pacing therapy. When conductive communication is maintained through the same electrodes as used for pacing, the system 100 may omit an antenna or telemetry coil in one or more of LPs 102 and 104.

In some embodiments, one or more LPs 102 and 104 can be co-implanted with the implantable cardioverter-defibrillator (ICD) 106. Each LP 102, 104 uses two or more electrodes located within, on, or within a few centimeters of the housing of the LP, for pacing and sensing at the cardiac chamber, for bidirectional communication with one another, with the programmer 109, and the ICD 106.

Figure 1B:
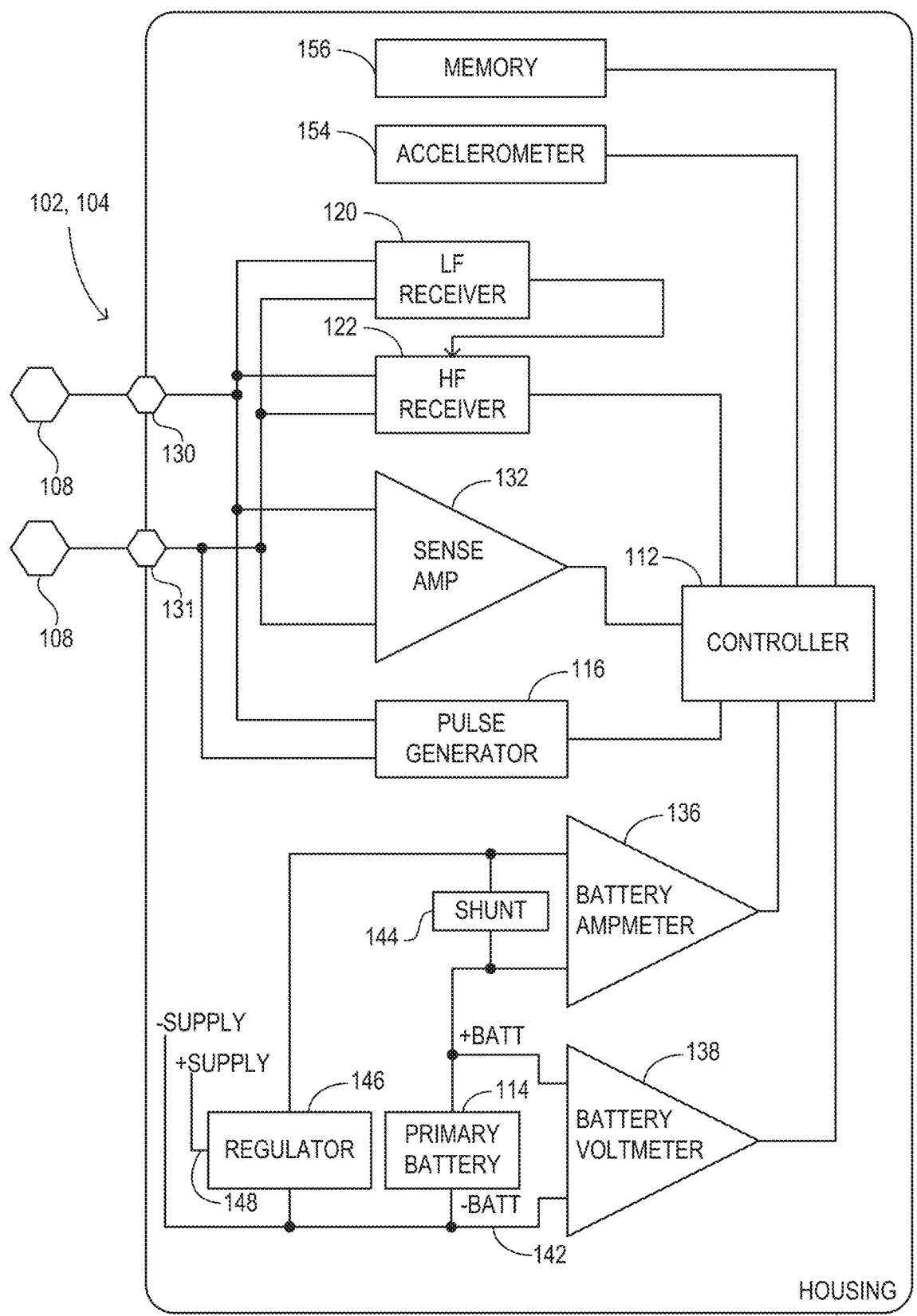
FIG. 1B is a block diagram of a single leadless pacemaker (LP) in accordance with certain embodiments herein.

Referring to FIG. 1B, a block diagram shows exemplary electronics within LPs 102 and 104. LP 102, 104 includes first and second receivers 120 and 122 that collectively define separate first and second communication channels 105 and 107 (FIG. 1A), (among other things) between LPs 102 and 104. Although first and second receivers 120 and 122 are depicted, in other embodiments, LP 102, 104 may only include first receiver 120, or may include additional receivers other than first and second receivers 120 and 122. As will be described in additional detail below, the pulse generator 116 can function as a transmitter that transmits implant-to-implant (i2i) communication signals using the electrodes 108. Usage of the electrodes 108 for communication enables the one or more LPs 102 and 104 to perform antenna-less and telemetry coil-less communication.

In accordance with certain embodiments, when one of the LPs 102 and 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

Still referring to FIG. 1B, each LP 102, 104 is shown as including a controller 112 and a pulse generator 116. The controller 112 can include, e.g., a microprocessor (or equivalent control circuitry), RAM and/or ROM memory, logic and timing circuitry, state machine circuitry, and I/O circuitry, but is not limited thereto. The controller 112 can further include, e.g., timing control circuitry to control the timing of the stimulation pulses (e.g., pacing rate, atrio-ventricular (AV) delay, atrial interconduction (A-A) delay, or ventricular interconduction (V-V) delay, etc.). Such timing control circuitry may also be used for the timing of refractory periods, blanking intervals, noise detection windows, evoked response windows, alert intervals, marker channel timing, and so on. The controller 112 can further include other dedicated circuitry and/or firmware/software components that assist in monitoring various conditions of the patient's heart and managing pacing therapies. The controller 112 and the pulse generator 116 may be configured to transmit event messages, via the electrodes 108, in a manner that does not inadvertently capture the heart in the chamber where LP 102, 104 is located, such as when the associated chamber is not in a refractory state. In addition, a LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, the programmer 109 may communicate over a programmer-to-LP channel, with LP 102, 104 utilizing the same communication scheme. The external programmer 109 may listen to the event message transmitted between LP 102, 104 and synchronize programmer to implant communication such that programmer 109 does not transmit communication signals 113 until after an implant to implant messaging sequence is completed.

In accordance with certain embodiments, LP 102, 104 may combine transmit operations with therapy. The transmit event marker may be configured to have similar characteristics in amplitude and pulse-width to a pacing pulse and LP 102, 104 may use the energy in the event messages to help capture the heart. For example, a pacing pulse may normally be delivered with pacing parameters of 2.5V amplitude, 500 ohm impedance, 60 bpm pacing rate, 0.4 ms pulse-width. The foregoing pacing parameters correspond to a current draw of about 1.9 pA. The same LP 102, 104 may implement an event message utilizing event signaling parameters for amplitude, pulse-width, pulse rate, etc. that correspond to a current draw of approximately 0.5 μA for transmit.

LP 102, 104 may combine the event message transmissions with pacing pulses. For example, LP 102, 104 may use a 50 μs wakeup transmit pulse having an amplitude of 2.5V which would draw 250 nC (nano Coulombs) for an electrode load of 500 ohm. The pulses of the transmit event message may be followed by an event message encoded with a sequence of short duration pulses (for example 16, 2 μs on/off bits) which would draw an additional 80 nC. The event message pulse would then be followed by the remaining pulse-width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102 or 104 senses an intrinsic event, it can send a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

Referring to FIG. 1B, the LP 102 (or 104) is shown as including an accelerometer 154 which can be hermetically contained within the housing 110. The accelerometer 154 can be any one of various different types of well known accelerometers, or can be a future developed accelerometer. For one example, the accelerometer 154 can be or include, e.g., a MEMS (micro-electromechanical system) multi-axis accelerometer of the type exploiting capacitive or optical cantilever beam techniques, or a piezoelectric accelerometer that employs the piezoelectric effect of certain materials to measure dynamic changes in mechanical variables. Where the accelerometer is a multi-axis accelerometer it can include two or three sensors aligned along orthogonal axes. Exemplary multi-axis accelerometers (also referred to as multi-dimensional accelerometers) that can be used are described in U.S. Pat. No. 6,658,292 (Kroll et al.) and U.S. Pat. No. 6,466,821 (Pianca et al.), each of which is incorporated herein by reference. For another example, a commercially available micro-electromechanical system (MEMS) accelerometer marketed as the ADXL345 by Analog Devices, Inc. (headquartered in Norwood, Mass.) is a three-axis accelerometer and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL345 includes a micro-machined accelerometer co-packaged with a signal processing IC.

Another commercially available MEMS accelerometer is the ADXL327 by Analog Devices, Inc., which is a small, thin, low power, complete three axis accelerometer with signal conditioned voltage outputs. In the ADXL327, the mechanical sensor and signal conditioning IC are packaged together. A further commercially available MEMS accelerometer that can be used is the LIS3DH three-axis accelerometer by STMicroelectronics (headquartered in Geneva, Switzerland). Additional and/or alternative types of accelerometers may also be used. For example, it is also within the scope of the present technology for the accelerometer 154 to be a beam-type of accelerometer, an example of which is described in U.S. Pat. No. 6,252,335 (Nilsson et al.), which is incorporated herein by reference.

The accelerometer 154 can be, e.g., a one-dimensional (1D) accelerometer (also known as a one-axis accelerometer), a two-dimensional (2D) accelerometer (also known as a two-axis accelerometer), or a three-dimensional (3D) accelerometer (also known as a three-axis accelerometer). A 1D accelerometer measures acceleration along one axis, e.g., the z-axis. A 2D accelerometer measures acceleration along two axes that are orthogonal to one another, e.g., the z-axis, and the x- or y-axis. A 3D accelerometer measures acceleration along three axes that are orthogonal to one another, e.g., the z-axis, the x-axis, and the y-axis. Each measure of acceleration (i.e., rate of change of velocity) can actually be a measure of proper acceleration, which is the rate of change of velocity of a body in its own instantaneous rest frame. For example, an accelerometer at rest on the surface of the Earth will measure an acceleration due to Earth's gravity, straight upwards (by definition) of g≈9.81 m/s^2.

Where an IMD (e.g., LP 102 or 104) includes an accelerometer within a housing of the IMD or attached thereto, the accelerometer can be used to measure the acceleration of the IMD along one or more axes, which measurement(s) can be used to determine the orientation of the IMD. Accordingly, because the output(s) of the accelerometer can be used to determine the orientation of the IMD, it can be said that the output(s) of the accelerometer (e.g., 154) are indicative of an orientation of the IMD (e.g., LP 102 or 104). More specifically, in accordance with certain embodiments, the controller 112 of an LP 102 (or 104) receives one or more outputs output(s) of the accelerometer 154, which is/are indicative of an orientation of the LP 102 (or 104). In such embodiments, the controller 112 can determine, based on the output(s) received from the accelerometer 154, an actual orientation of the LP 102 (or 104). Each output of the accelerometer 154 can comprise a respective signal. One or more signals produced and output by the accelerometer 154 can be used by the LP (the includes the accelerometer) to determine a posture of the patient, e.g., to determine whether the patient is supine (i.e., lying down) or upright (e.g., standing or sitting), but is not limited thereto.

The one or more signals output by the accelerometer 154 can be analyzed by the controller 112 and/or other circuitry. In certain embodiments, the accelerometer 154 is packaged along with an integrated circuit (IC) that is designed to analyze the signal(s) it generates. In such embodiments, one or more outputs of the packaged sensor/IC can be an indication of acceleration along one or more axes. In other embodiments, the accelerometer 154 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the controller 112 or other circuitry can read the digital data from the memory and analyze the digital data. Other variations are also possible, and within the scope of embodiments of the present technology.

Still referring to FIG. 1B, the LP 102 (or 104) is shown as including a memory 156. The programmable operating parameters used by controller 112 can be stored in the memory 156 and used to customize the operation of LP 102 (or 104) to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. One or more morphology templates described herein can also be stored in the memory 156.

FIG. 1B depicts a single LP 102 (or 104) and shows the LP's functional elements substantially enclosed in a hermetic housing 110. The LP 102 (or 104) has at least two electrodes 108 located within, on, or near the housing 110, for delivering pacing pulses to and sensing electrical activity from the muscle of the cardiac chamber, for sensing motion, for sensing temperature, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, receivers 120, 122 for receiving information from at least one other device via the electrodes 108, and the pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

The electrodes 108 can be configured to communicate bidirectionally among the multiple LPs and/or the implanted ICD 106 to coordinate pacing pulse delivery and optionally other therapeutic or diagnostic features using messages that identify an event at an individual LP originating the message and an LP receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more LPs 102, 104 and/or the ICD 106 and transmit data including designated codes for events detected or created by an individual LP. Individual LPs can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other LPs via the event message coded pacing pulse. The pacemaker or pacemakers receiving the message are adapted to respond to the message in a predetermined manner depending on type and location of the event.

Moreover, information communicated on the incoming channel can also include an event message from another leadless cardiac pacemaker signifying that the other leadless cardiac pacemaker has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another LP, or to the ICD, that the sending leadless cardiac pacemaker has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to LPs 102, 104 configured for implantation in electrical contact with a cardiac chamber and for performing cardiac rhythm management functions in combination with the implantable ICD 106. The implantable ICD 106 and the one or more LPs 102, 104 can be configured for leadless intercommunication by information conduction through body tissue and/or wireless transmission between transmitters and receivers in accordance with the discussed herein. As mentioned above, the ICD 106 can include its own motion sensor and/or temperature sensor.

As shown in the illustrative embodiments, an LP 102, 104 can comprise two or more leadless electrodes 108 configured for delivering cardiac pacing pulses, sensing evoked and/or natural cardiac electrical signals, and bidirectionally communicating with the co-implanted ICD 106.

LP 102, 104 can be configured for operation in a particular location and a particular functionality at manufacture and/or at programming by an external programmer 109. Bidirectional communication among the multiple leadless cardiac pacemakers can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, or one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking and refractory periods, etc. Accordingly, each LP preferably knows an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs. ACapConfirm, sensing sensitivities, etc.).

Also shown in FIG. 1B, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the controller 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102, 104 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another leadless cardiac pacemaker for usage as a signature for determining triggering information validity and, for a signature arriving within predetermined limits, activating delivery of a pacing pulse following a predetermined delay of zero or more milliseconds.

In certain embodiments, the electrodes of an LP 102, 104 can be used to sense an electrocardiogram (EGM) from which atrial and/or ventricular activity can be detected, e.g., by detecting QRS complexes and/or P waves. Such an EGM can also be used by an LP 102, 104 for capture analysis, as will be described in additional detail below. For the remaining discussion, unless stated otherwise, it is assumed that the LP 102 is implanted in the right atrium, and thus, can be referred to as the aLP, and that the LP 104 is implanted in the right ventricle, and thus, can be referred to as the vLP. The EGM sensed by the aLP, using at least two of its electrodes 108, can be referred to more specifically as an atrial EGM (aEGM). The EGM sensed by the vLP, using at least two of its electrodes 108, can be referred to more specifically as a ventricular EGM (vEGM).

Figure 2:
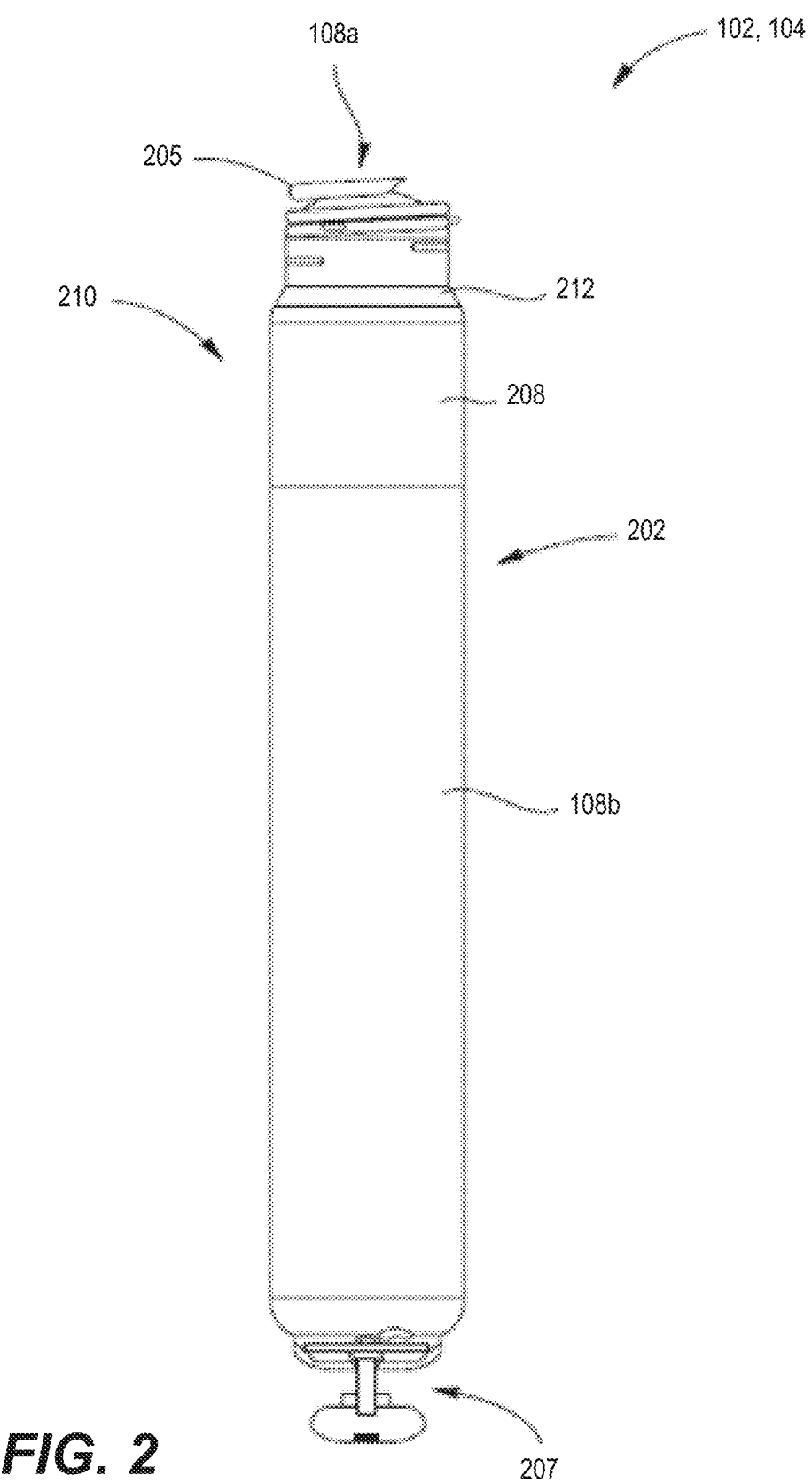
FIG. 2 illustrates an LP in accordance with certain embodiments herein.

FIG. 2 shows an LP 102, 104. The LP can include a hermetic housing 202 (e.g., the housing 110 in FIG. 1) with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue. The electrodes 108a and 108b are examples of the electrodes 108 shown in and discussed above with reference to FIG. 1B. One of the electrodes 108 (e.g., 108a) can function as a cathode type electrode and another one of the electrodes 108 (e.g., 108b) can function as an anode type electrode, or vice versa, when the electrodes are used for delivering stimulation.

The housing 202 can also include an electronics compartment 210 within the housing that contains the electronic components necessary for operation of the pacemaker, including, e.g., a pulse generator, receiver, a battery, and a processor for operation. The hermetic housing 202 can be adapted to be implanted on or in a human heart, and can be cylindrically shaped, rectangular, spherical, or any other appropriate shapes, for example.

The housing 202 can comprise a conductive, biocompatible, inert, and anodically safe material such as titanium, 316L stainless steel, or other similar materials. The housing 202 can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 2, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 2, the pacemaker can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 2, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 2) into contact with stimulable tissue. Electrode 108b can serve as an indifferent electrode for sensing and pacing.

The fixation mechanism may be coated partially or in full for electrical insulation, and a steroid-eluting matrix may be included on or near the device to minimize fibrotic reaction, as is known in conventional pacing electrode-leads.

Implant-to-Implant Event Messaging

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Figure 3:
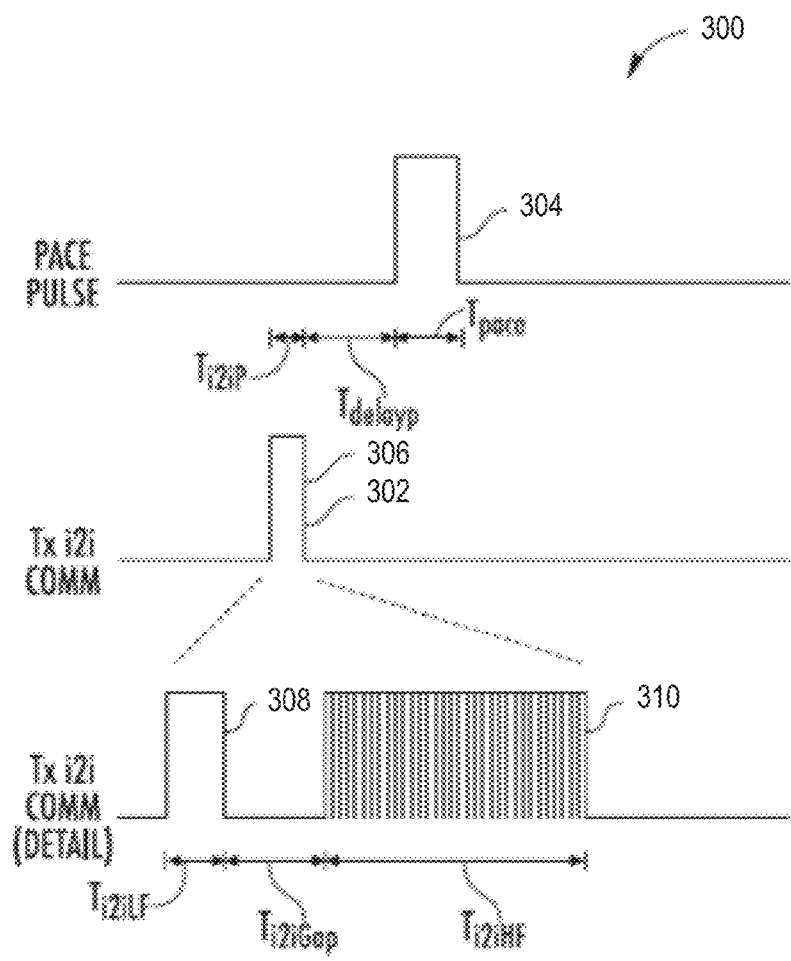
FIG. 3 is a timing diagram demonstrating one embodiment of implant to implant (i2i) communication for a paced event.

FIG. 3 is a timing diagram 300 demonstrating one example of an i2i communication for a paced event. The i2i communication may be transmitted, for example, from LP 102 to LP 104. As shown in FIG. 3, in this embodiment, an i2i transmission 302 is sent prior to delivery of a pace pulse 304 by the transmitting LP (e.g., LP 102). This enables the receiving LP (e.g., LP 104) to prepare for the remote delivery of the pace pulse. The i2i transmission 302 includes an envelope 306 that may include one or more individual pulses. For example, in this embodiment, envelope 306 includes a low frequency pulse 308 followed by a high frequency pulse train 310. Low frequency pulse 308 lasts for a period Ti2iLF, and high frequency pulse train 310 lasts for a period Ti2iHF. The end of low frequency pulse 308 and the beginning of high frequency pulse train 310 are separated by a gap period, Ti2iGap.

As shown in FIG. 3, the i2i transmission 302 lasts for a period Ti2iP, and pace pulse 304 lasts for a period Tpace. The end of i2i transmission 302 and the beginning of pace pulse 304 are separated by a delay period, TdelayP. The delay period may be, for example, between approximately 0.0 and 10.0 milliseconds (ms), particularly between approximately 0.1 ms and 2.0 ms, and more particularly approximately 1.0 ms. The term approximately, as used herein, means +/−10% of a specified value.

Figure 4:
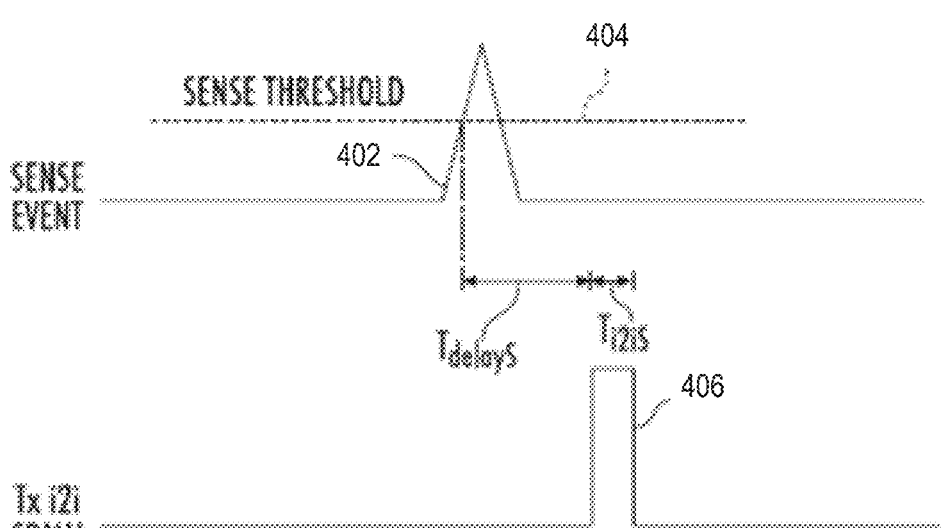
FIG. 4 is a timing diagram demonstrating one embodiment of i2i communication for a sensed event.

FIG. 4 is a timing diagram 400 demonstrating one example of an i2i communication for a sensed event. The i2i communication may be transmitted, for example, from LP 102 to LP 104. As shown in FIG. 4, in this embodiment, the transmitting LP (e.g., LP 102) detects the sensed event when a sensed intrinsic activation 402 crosses a sense threshold 404. A predetermined delay period, TdelayS, after the detection, the transmitting LP transmits an i2i transmission 406 that lasts a predetermined period Ti2iS. The delay period may be, for example, between approximately 0.0 and 10.0 milliseconds (ms), particularly between approximately 0.1 ms and 2.0 ms, and more particularly approximately 1.0 ms.

As with i2i transmission 302, i2i transmission 406 may include an envelope that may include one or more individual pulses. For example, similar to envelope 406, the envelope of i2i transmission 406 may include a low frequency pulse followed by a high frequency pulse train.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conducted communication of markers/commands in the event messages (per i2i communication protocol). As explained above, conducted communication represents event messages transmitted from the sensing/pacing electrodes at frequencies outside the RF or Wi-Fi frequency range. Alternatively, the event messages may be conveyed over communication channels operating in the RF or Wi-Fi frequency range. The figures and corresponding description below illustrate non-limiting examples of markers that may be transmitted in event messages. The figures and corresponding description below also include the description of the markers and examples of results that occur in the LP that receives the event message. Table 1 represents exemplary event markers sent from the aLP to the vLP, while Table 2 represents exemplary event markers sent from the vLP to the aLP. In the master/slave configuration, AS event markers are sent from the aLP each time that an atrial event is sensed outside of the post ventricular atrial blanking (PVAB) interval or some other alternatively-defined atrial blanking period. The AP event markers are sent from the aLP each time that the aLP delivers a pacing pulse in the atrium. The aLP may restrict transmission of AS markers, whereby the aLP transmits AS event markers when atrial events are sensed both outside of the PVAB interval and outside the post ventricular atrial refractory period (PVARP) or some other alternatively-defined atrial refractory period. Alternatively, the aLP may not restrict transmission of AS event markers based on the PVARP, but instead transmit the AS event marker every time an atrial event is sensed.

TABLE 1

"A2V" Markers/Commands (i.e., from aLP to vLP)

| Marker | Description | Result in vLP |
|---|---|---|
| AS | Notification of a sensed event in atrium (if not in PVAB or PVARP) | Initiate AV interval (if not in PVAB or PVARP) |
| AP | Notification of a paced event in atrium | Initiate PAVB Initiate AV interval (if not in PVARP) |

As shown in Table 1, when an aLP transmits an event message that includes an AS event marker (indicating that the aLP sensed an intrinsic atrial event), the vLP initiates an AV interval timer. If the aLP transmits an AS event marker for all sensed events, then the vLP would preferably first determine that a PVAB or PVARP interval is not active before initiating an AV interval timer. If however the aLP transmits an AS event marker only when an intrinsic signal is sensed outside of a PVAB or PVARP interval, then the vLP could initiate the AV interval timer upon receiving an AS event marker without first checking the PVAB or PVARP status. When the aLP transmits an AP event marker (indicating that the aLP delivered or is about to deliver a pace pulse to the atrium), the vLP initiates a PVAB timer and an AV interval time, provided that a PVARP interval is not active. The vLP may also blank its sense amplifiers to prevent possible crosstalk sensing of the remote pace pulse delivered by the aLP.

TABLE 2

"V2A" Markers/Commands (i.e., from vLP to aLP)

| Marker | Description | Result in aLP |
|---|---|---|
| VS | Notification of a sensed event in ventricle | Initiate PVARP |
| VP | Notification of a paced event in ventricle | Initiate PVAB Initiate PVARP |
| AP | Command to deliver immediate pace pulse in atrium | Deliver immediate pace pulse to atrium |

As shown in Table 2, when the vLP senses a ventricular event, the vLP transmits an event message including a VS event marker, in response to which the aLP may initiate a PVARP interval timer. When the vLP delivers or is about to deliver a pace pulse in the ventricle, the vLP transmits VP event marker. When the aLP receives the VP event marker, the aLP initiates the PVAB interval timer and also the PVARP interval timer. The aLP may also blank its sense amplifiers to prevent possible crosstalk sensing of the remote pace pulse delivered by the vLP. The vLP may also transmit an event message containing an AP command marker to command the aLP to deliver an immediate pacing pulse in the atrium upon receipt of the command without delay.

The foregoing event markers are examples of a subset of markers that may be used to enable the aLP and vLP to maintain full dual chamber functionality. In one embodiment, the vLP may perform all dual-chamber algorithms, while the aLP may perform atrial-based hardware-related functions, such as PVAB, implemented locally within the aLP. In this embodiment, the aLP is effectively treated as a remote 'wireless' atrial pace/sense electrode. In another embodiment, the vLP may perform most but not all dual-chamber algorithms, while the aLP may perform a subset of diagnostic and therapeutic algorithms. In an alternative embodiment, vLP and aLP may equally perform diagnostic and therapeutic algorithms. In certain embodiments, decision responsibilities may be partitioned separately to one of the aLP or vLP. In other embodiments, decision responsibilities may involve joint inputs and responsibilities.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a VVI mode as the vLP does not depend on i2i communication to perform ventricular pace/sense activities. Once i2i communication is restored, the system 100 can automatically resume dual-chamber functionalities.

Atrial Capture Monitoring

Confirmation of pacing capture is important when performing cardiac pacing to ensure safety and atrial-ventricular (AV) synchronization. For example, when performing DDD pacing, the vLP should pace the RV at a specified AV delay following when the aLP paced the RA.

Certain embodiments of the present technology described herein can be used to determine whether atrial capture occurred (responsive to a pacing a pulse delivered by an aLP) based on a vEGM sensed by a vLP. In other words, in such embodiments, it is the vLP rather than the aLP that monitors for atrial capture.

Monitoring for atrial capture using the vLP may be preferred to monitoring for atrial capture using the aLP that delivered the pacing pulse in the first place. This is because where an LP (e.g., the aLP) uses the same electrodes to sense an EGM that the LP uses to deliver a pacing pulse, the electrodes will be polarized for a period of time following delivery of the pacing pulse, thereby making it difficult to monitor for capture (responsive to the pacing pulse) within the sensed EGM (e.g., the aEGM). By contrast, where a remote LP (e.g., the vLP) is also implanted in a patient, and the electrodes of the remote LP are not polarized when the local LP (e.g., the aLP) delivers the pacing pulse, the remote LP may be in a better condition and position to monitor for capture.

More specifically, in accordance with certain embodiments of the present technology, for use with an implantable system including an atrial leadless pacemaker (aLP) and a ventricular leadless pacemaker (vLP), the vLP uses a ventricular EGM (vEGM) obtained by the vLP to determine whether or not a pacing pulse delivered by the aLP resulted in atrial capture. The vEGM obtained by the vLP includes both near-field (NF) components corresponding to ventricular electrical activity, and far-field (FF) components corresponding to atrial electrical activity. In other words, the vEGM obtained by the vLP includes both near-field ventricular and far-field atrial signals.

When a pacing pulse delivered to the atrium by the aLP successfully captures atrial tissue, the atrium activates following a unique pattern determined by the location of the aLP. This activation pattern is different from that of an intrinsic sinus beat (also referred to as an intrinsic atrial activation), which would result in differences in the morphology of the far-field atrial signal. Certain embodiments of the present technology utilize such differences in the morphology of the far-field atrial signal to determine whether or not atrial capture occurs responsive to an atrial pacing pulse. More specifically, in accordance with certain embodiments, a vLP monitors a vEGM obtained by the vLP in real time and determines an atrial capture outcome based on the morphology and timing of the far-field signal after atrial pacing stimulus.

In accordance with specific embodiments, three distinct features are extracted from a vEGM with respect to the atrial activities, which three distinct features are described below with reference to FIG. 5, wherein the signal waveform 500 is an example vEGM signal obtained by a vLP (e.g., 104). Also shown in FIG. 5, as a reference, is a surface electrocardiogram (ECG) 501 obtained from an ECG lead 1.

Figure 5:
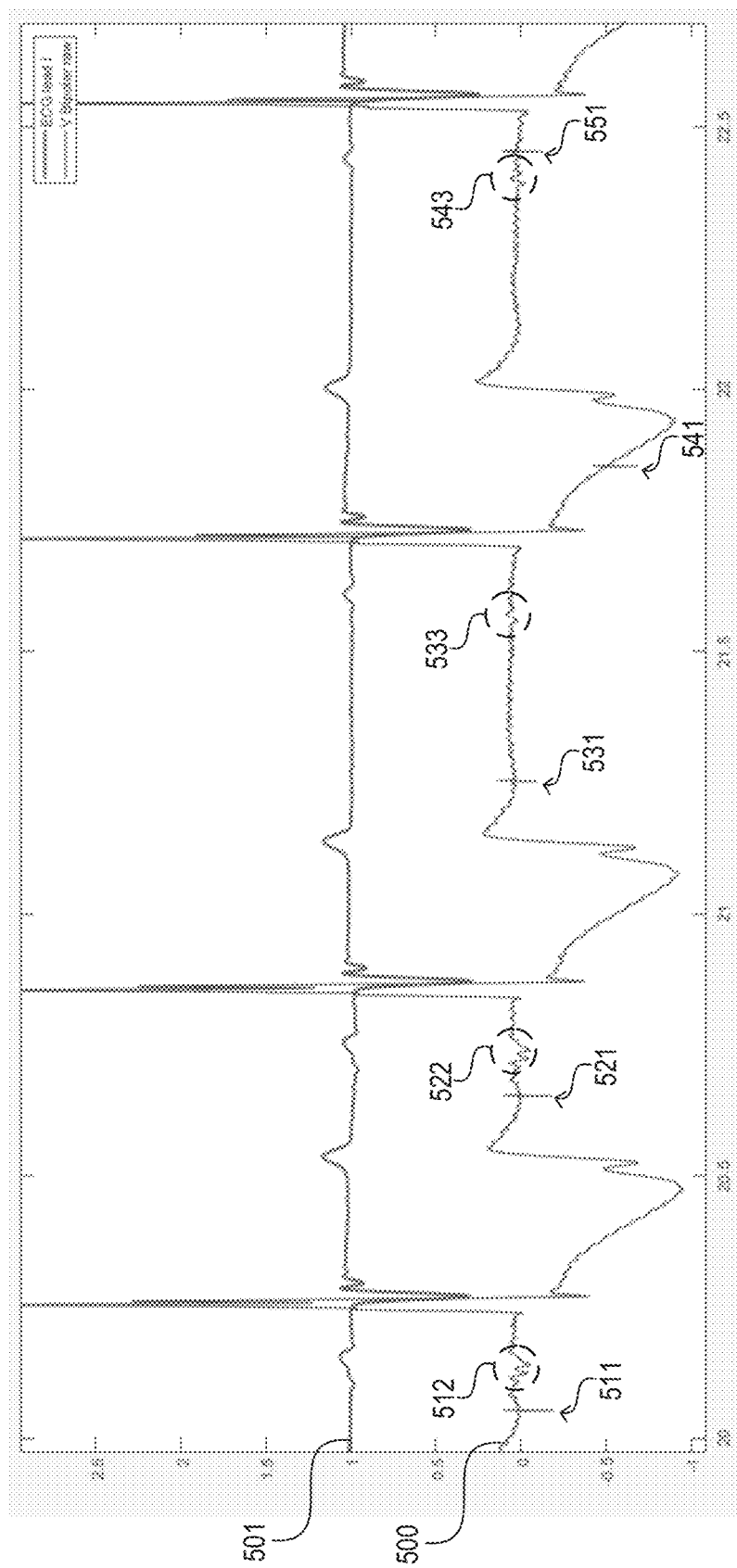
FIG. 5 illustrates an exemplary vEGM and three distinct features that can be extracted from the vEGM with respect to the atrial activities. Also shown in FIG. 5, as a reference, is a corresponding example surface ECG obtained from an ECG lead 1.

Referring to FIG. 5, within the vEGM are shown five atrial pacing artifacts labeled 511, 521, 531, 541, and 551, wherein each of the atrial pacing artifacts includes short sharp spikes, and more specifically, both a short sharp upward spike and a short sharp downward spike that collectively resemble a vertical line. In this particular example, the atrial pacing pulses that caused the atrial pacing artifacts 511 and 521 were 1.0 volt (V) pacing pulses that resulted in atrial capture, and the atrial pacing pulses that caused the atrial pacing artifacts 531, 541, and 551 were 0.5 V pacing pulses that failed to cause atrial capture. The portions of the vEGM 500 that are labeled 512 and 522 (and which respectively follow the atrial pacing artifacts 511 and 521) are distinct features corresponding to paced atrial activation, and thus, are indicative atrial capture responsive to atrial pacing pulses. By contrast, the portions of the vEGM 500 that are labeled 533 and 543 (and which respectively follow the atrial pacing artifacts 531 and 541) are distinct features corresponding to intrinsic atrial activation, and thus, are indicative of failed atrial capture responsive to atrial pacing pulses.

In accordance with certain embodiments, various types of morphology templates are acquired, including an atrial pacing artifact morphology template, a paced atrial activation morphology template, and an intrinsic atrial activation morphology template. Such templates can be obtained at implant or at other in-clinic sessions and saved it in the vLP for reference. More or less templates can alternatively be obtained and saved in the vLP for references.

The atrial pacing artifact morphology template corresponds to far-field atrial signal components expected to be present in a vEGM sensed by the vLP when an atrial pacing pulse is delivered by the aLP. Such an atrial pacing artifact morphology template can be obtained by storing a segment of a vEGM (sensed by the vLP) that corresponds to a window of time within which it is known the aLP delivered a pacing pulse. In certain embodiments, multiple such segments are obtained and averaged to produce the atrial pacing artifact morphology template.

The paced atrial activation morphology template corresponds to far-field atrial signal components expected to be present in a vEGM sensed by the vLP when an atrial pacing pulse delivered by the aLP captures atrial tissue. Such an atrial pacing artifact morphology template can be obtained by storing a segment of a vEGM (sensed by the vLP) that corresponds to a window of time within which it is known that atrial capture occurred responsive to the aLP delivered a pacing pulse. In certain embodiments, multiple such segments are obtained and averaged to produce the paced atrial activation morphology template. The paced atrial activation morphology template can also be referred to as an atrial capture confirmation template, since it is used to confirm whether atrial capture occurred.

The intrinsic atrial activation morphology template corresponds to far-field atrial signal components expected to be present in a vEGM sensed by the vLP when there is an intrinsic atrial activation. Such an intrinsic atrial activation morphology template can be obtained by storing a segment of a vEGM (sensed by the vLP) that corresponds to a window of time within which it is known that an intrinsic atrial activation occurred. In certain embodiments, multiple such segments are obtained and averaged to produce the intrinsic atrial activation morphology template.

Figure 6:
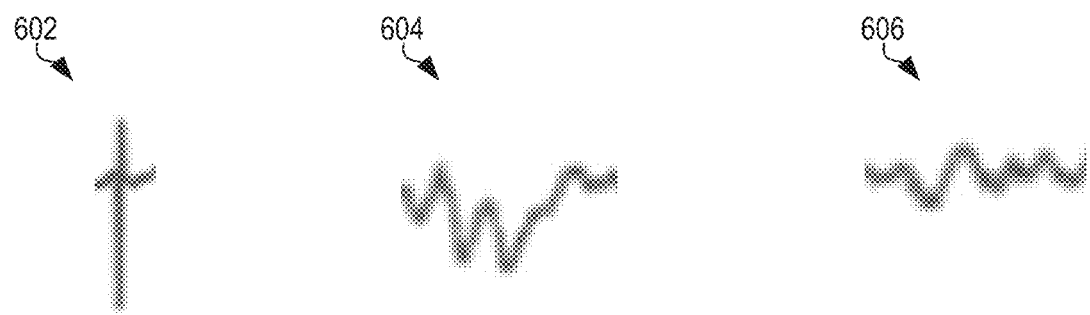
FIG. 6 illustrates exemplary morphology templates, including an atrial pacing artifact morphology template, a paced atrial activation morphology template, and an intrinsic atrial activation morphology template.

FIG. 6 illustrates exemplary morphology templates, including an atrial pacing artifact morphology template 602, a paced atrial activation morphology template 604, and an intrinsic atrial activation morphology template 606. Accordingly, FIG. 6 shows examples of three different types of morphology templates.

In certain embodiments, a single atrial pacing artifact morphology template (e.g., 602), a single paced atrial activation morphology template (e.g., 604), and a single intrinsic atrial activation morphology template (e.g., 606) can be stored in the memory (e.g., 156) of a vLP (e.g., 104) and used regardless of the posture of a patient. In other words, for each different type of morphology template, one respective morphology template can be stored and used to monitor for atrial capture.

In alternative embodiments, for one or more of the different types of morphology templates stored in the memory of the vLP there are at least first and second versions of the morphology template, wherein the first version is to be used when the patient has a first posture, and the second version is to be used when the patient has a second posture. The first posture can be, e.g., supine (i.e., lying down), and the second posture can be, e.g., an upright position. An accelerometer (e.g., 154) or other sensor of the vLP can monitor a posture of a patient, and the vLP (or more specifically, a processor or controller thereof) can select which version of the morphology templates are to be compared to the morphology of a portion of a sensed vEGM to thereby determine whether a match therebetween is detected. More than two different types of postures can be monitored for. For a more specific example, stored within the memory of the vLP can be a first atrial pacing artifact morphology template for use when the patient is upright, a second atrial pacing artifact morphology template for use when the patient is supine, a first atrial activation morphology template for use when the patient is upright, a second atrial activation morphology template for use when the patient is supine, a first intrinsic atrial activation morphology template for use when the patient is upright, and a second intrinsic atrial activation morphology template for use when the patient is supine. Such templates can be obtained at implant or at other in-clinic sessions and saved in the memory of the vLP for reference. Where an accelerometer (e.g., 154) and/or other type of sensor is used to monitor for more than two types of postures, more than two morphology templates can be obtained and saved for each of one or more different types of morphology templates.

In certain embodiments morphology templates can be automatically updated from time-to-time by the vLP. For example, by taking a moving average of events that are classified as pacing artifacts, paced atrial activations, and intrinsic atrial activations, respectively. The updated templates may be applied periodically (e.g. weekly) to accommodate any gradual changes in the such morphologies. Such morphology updates can be performed for each version of each type of morphology template, or just for specific types and/or versions of morphology templates that are expected to change over time. For example, it may not be necessary to update a pacing artifact morphology template if it is determined, through clinical analysis, that the pacing artifact morphology template rarely and/or minimally changes. By contrast, it would likely be more beneficial to update over time one or more versions of the paced atrial activation morphology template and/or the intrinsic atrial activation morphology template.

Figure 7A:
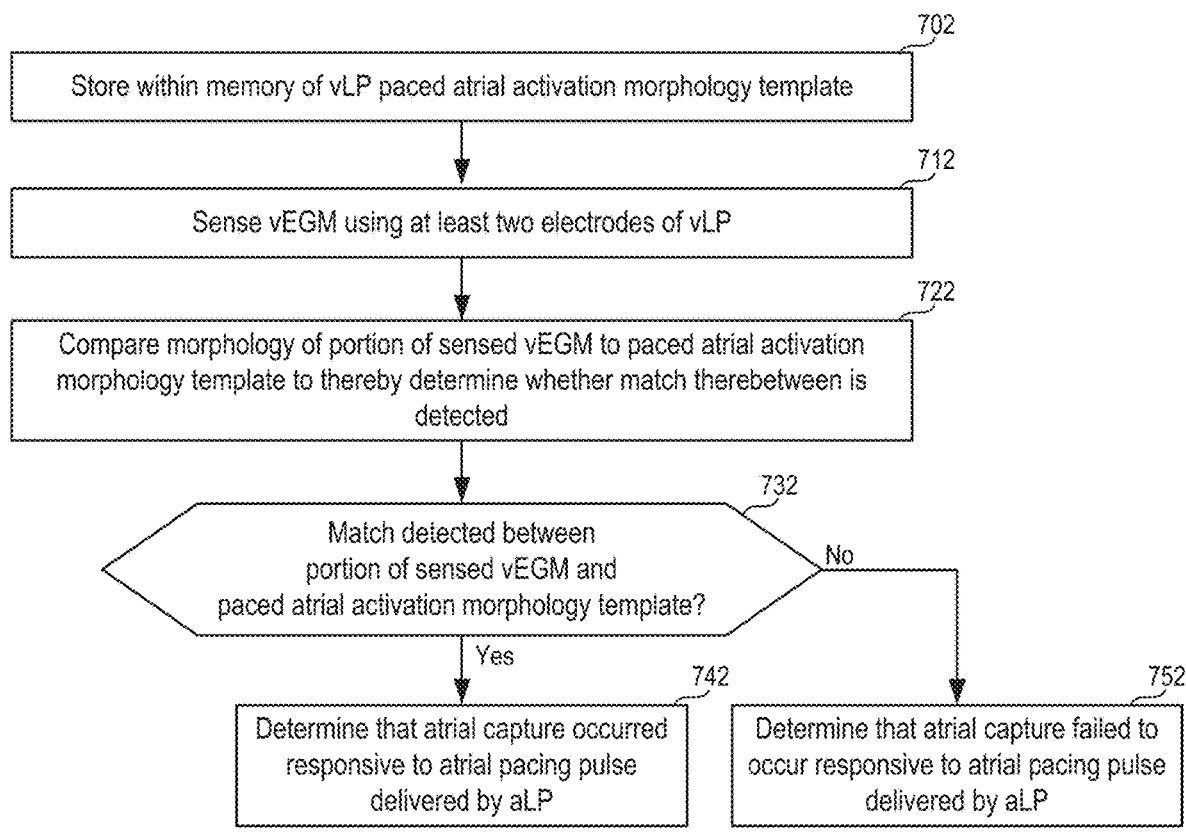
FIGS. 7A, 7B and 7C are high level flow diagrams that are used to summarize methods according to various embodiments of the present technology that can be used to monitor for atrial capture that is responsive to an atrial pacing pulse delivered by an atrial leadless pacemaker.
Figure 7B:
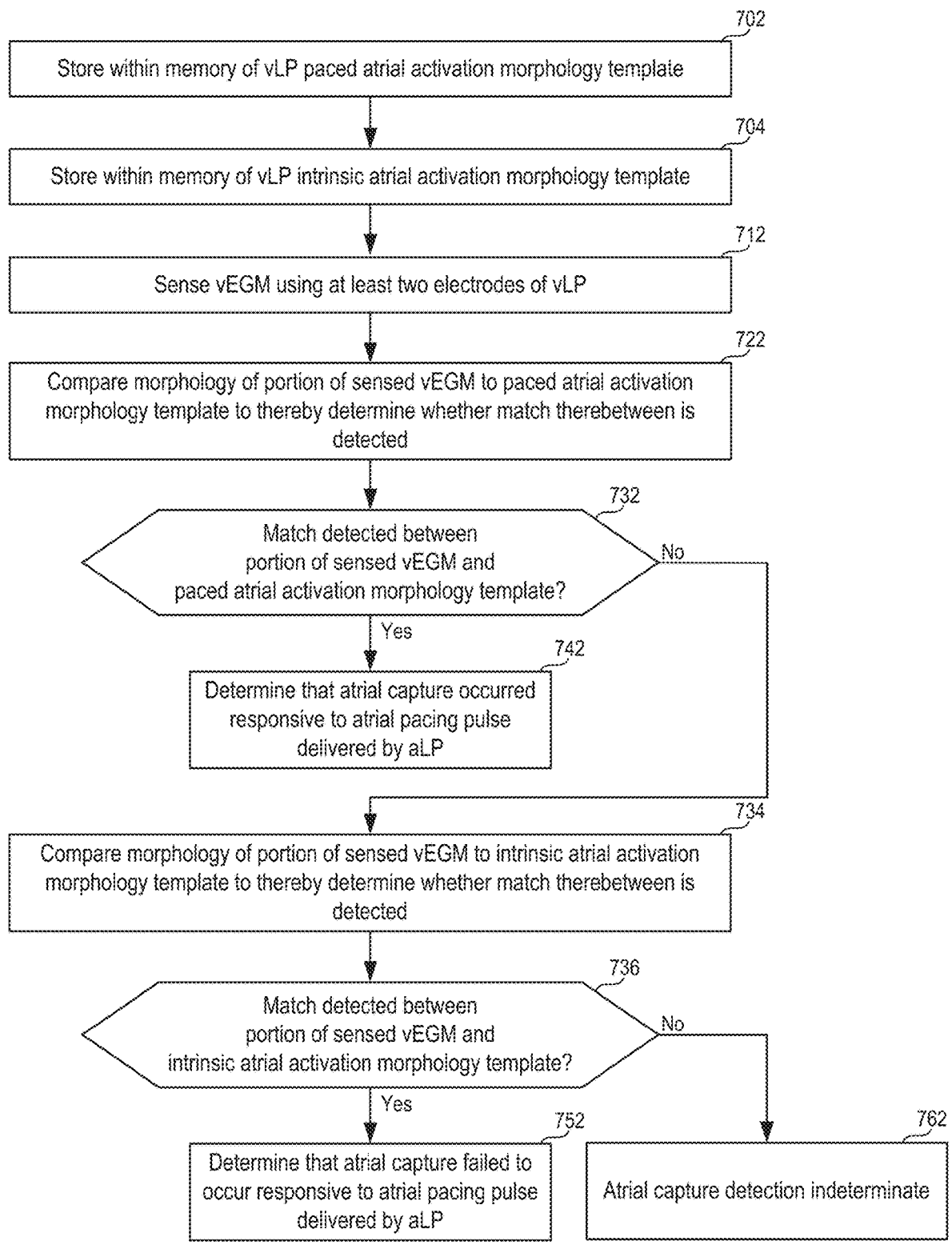
Figure 7C:
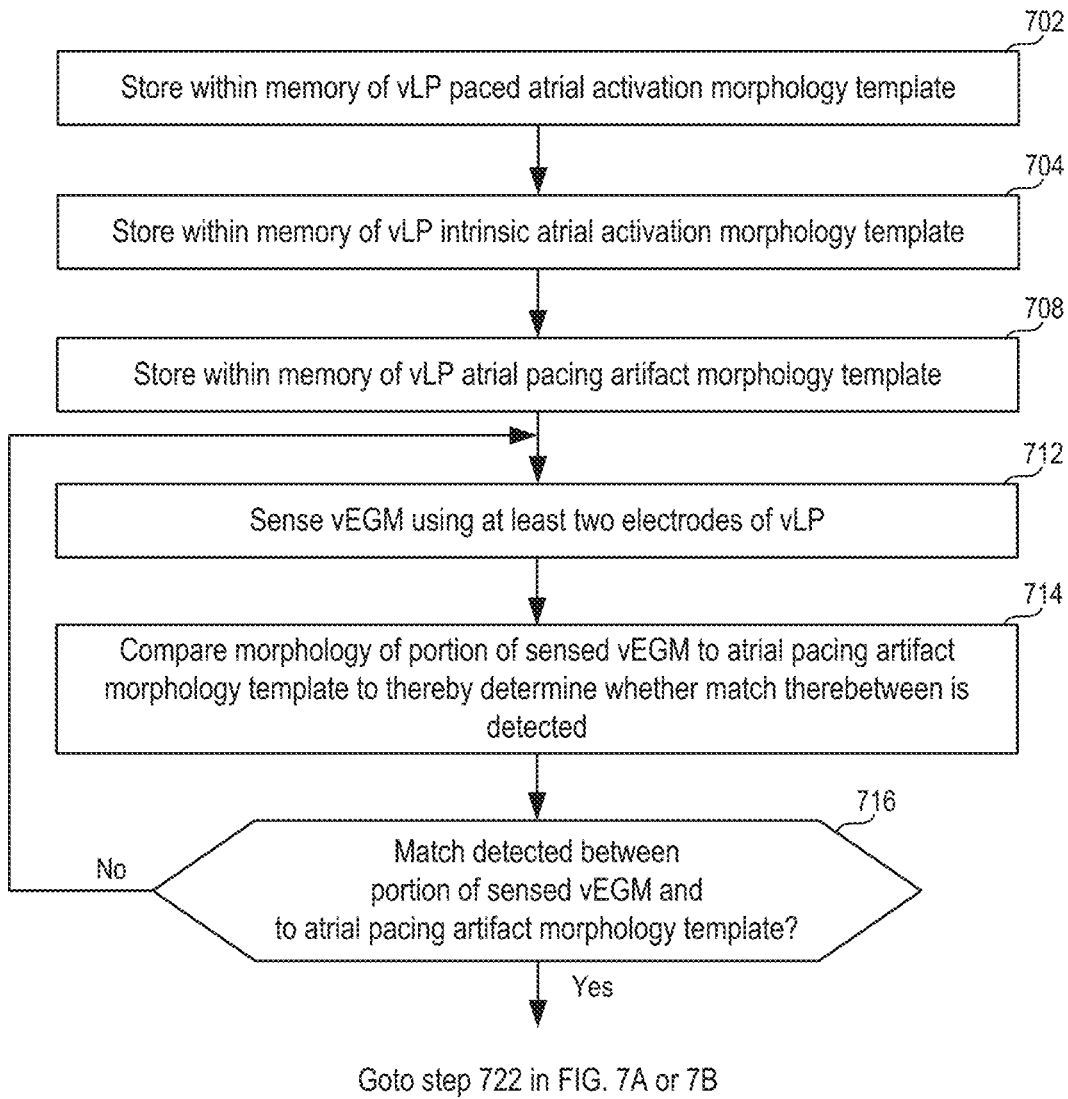

The high level flow diagrams of FIGS. 7A-7C will now be used to describe various different techniques that a vLP (e.g., 104) can use to monitor for atrial capture, and more specifically, to determine whether or not a pacing pulse delivered by an aLP (e.g., 102) caused atrial capture. Such embodiments can be more generally used within implantable system including an aLP and vLP.

Referring to FIG. 7A, step 702 involves storing within a memory of the vLP a paced atrial activation morphology template corresponding to far-field atrial signal components expected to be present in a vEGM sensed by the vLP when an atrial pacing pulse delivered by the aLP captures atrial tissue. An example of such a paced atrial activation morphology template is the template 604 shown in FIG. 6.

Still referring to FIG. 7A, step 712 involves sensing a vEGM using at least two electrodes of the vLP. Examples of electrodes that can be used to sense the vEGM are the electrodes 108 discussed above with reference to FIGS. 1B and 2. An example of a vEGM is the vEGM 500 shown in FIG. 5 discussed above.

Still referring to FIG. 7A, step 722 involves comparing a morphology of a portion of the sensed vEGM to the paced atrial activation morphology template to thereby determine whether a match therebetween is detected.

Step 732 is a decision block or step, which directs flow to step 742 or to step 752, depending upon the results of step 732. More specifically, at step 732 there is a determination of whether or not a morphology of a portion of the sensed vEGM matched the paced atrial activation morphology template. If the answer to the determination at step 732 is Yes, then flow goes to step 742 and it is concluded that atrial capture occurred, and more specifically, was detected. However, if the answer to the determination at step 732 is No, then flow goes to step 752 and it is concluded that atrial capture failed to occur, and more specifically, was not detected. While steps 722 and 732 are shown as two distinct steps in FIG. 7A, these steps can alternatively be combined into a single step, as would be appreciated by one skilled in the art.

Another embodiment that a vLP (e.g., 104) can use to monitor for atrial capture, and more specifically, to determine whether or not a pacing pulse delivered by an aLP (e.g., 102) caused atrial capture, will now be described with reference to FIG. 7B. Steps in FIG. 7B that are the same as the were in FIG. 7A are labeled the same, and are discussed in less detail with reference to FIG. 7B, since reference can be made to the above discussion of FIG. 7A.

Referring to FIG. 7B, step 702 involves storing within a memory of the vLP a paced atrial activation morphology template, which step is the same as it was in FIG. 7A, and thus need not be described again. Step 704 involves storing within the memory of the vLP an intrinsic atrial activation morphology template corresponding to far-field atrial signal components expected to be present in a vEGM sensed by the vLP when an intrinsic atrial activation occurs. While steps 702 and 704 are shown as separate steps, such steps can be combined into a single step, as would be appreciated by one of skill in the art.

Still referring to FIG. 7B, step 712 involves sensing a vEGM using at least two electrodes of the vLP. Since step 712 in FIG. 7B is the same as it was in FIG. 7A it need not be described again.

Still referring to FIG. 7B, step 722 involves comparing a morphology of a portion of the sensed vEGM to the paced atrial activation morphology template to thereby determine whether a match therebetween is detected.

Step 732 is a decision block or step, which directs flow to step 742 or to step 752, depending upon the results of step 732. More specifically, at step 732 there is a determination of whether or not a morphology of a portion of the sensed vEGM matched the paced atrial activation morphology template. If the answer to the determination at step 732 is Yes, then flow goes to step 742 and it is concluded that atrial capture occurred, and more specifically, was detected. However, if the answer to the determination at step 732 is No, then flow goes to step 734.

Step 734 involves comparing a morphology of a portion of the sensed vEGM to the intrinsic atrial activation morphology template to thereby determine whether a match therebetween is detected.

Step 736 is a decision block or step, which directs flow to step 752 or to step 762, depending upon the results of step 734. More specifically, at step 736 there is a determination of whether or not a morphology of a portion of the sensed vEGM matched the intrinsic atrial activation morphology template. If the answer to the determination at step 736 is Yes, then flow goes to step 752 and it is concluded that atrial capture failed to occur (because an intrinsic atrial activation was detected, rather than a paced atrial activation). However, if the answer to the determination at step 734 is No, then flow goes to step 762 and the atrial capture detection is found to be indeterminate. More generally, step 762 occurs if the vLP neither detects a match with the paced atrial activation morphology template nor a match with the intrinsic atrial activation morphology template.

In the embodiment described with reference to FIG. 7B, the vLP concludes that atrial capture (responsive to an atrial pacing pulsed delivered by the aLP) failed to occur if there was no match between a portion of the vEGM and the paced atrial activation morphology template, and if there was a match between a portion of the vEGM and the intrinsic atrial activation template. In other words, in the embodiment described with reference to FIG. 7B, there are two conditions that need to be true for the vLP to conclude that atrial capture failed to occur. In an alternative embodiments, the vLP need only detect one of those two conditions to conclude that atrial capture failed to occur. More specifically, in such an alternative embodiment the vLP can conclude that atrial capture failed to occur if there was no match between a portion of the vEGM and the paced atrial activation morphology template, or if there was a match between a portion of the vEGM and the intrinsic atrial activation template.

The portion of the vEGM that the vLP analyzes the morphology of (e.g., at step 722, or at steps 722 and 734) can be determined in various different manners. For example, in the embodiment described with reference to FIG. 7C, the portion of the vEGM that the vLP analyzes the morphology of (e.g., at step 722, or at steps 722 and 734) can correspond to a window following when the vLP detects that the aLP has delivered an atrial pacing pulse to the atrium. The duration of such window can be in the range of about 150 to 250 milliseconds (ms), but is not limited thereto.

Referring to FIG. 7C, step 702 involves storing within a memory of the vLP a paced atrial activation morphology template, and step 704 involves storing within the memory of the vLP an intrinsic atrial activation morphology template. Since steps 702 and 704 are the same as the were in FIG. 7B, they need not be described again. Step 706 involves storing within the memory of the vLP an atrial pacing artifact morphology template corresponding to far-field atrial signal components expected to be present in a vEGM sensed by the vLP when an aLP delivers an atrial pacing pulse to the atrium. While steps 702, 704, and 706 are shown as separate steps, two or all of these steps can be combined into a single step, as would be appreciated by one of skill in the art. It would also be possible to change the order of steps 702, 704, and 706.

Still referring to FIG. 7C, step 712 involves sensing a vEGM using at least two electrodes of the vLP. Since step 712 in FIG. 7B is the same as it was in FIGS. 7A and 7B it need not be described again.

Still referring to FIG. 7C, step 714 involves comparing a morphology of a portion of the sensed vEGM to the atrial pacing artifact morphology template to thereby determine whether a match therebetween is detected.

Step 716 is a decision block or step. More specifically, at step 716 there is a determination of whether or not a morphology of a portion of the sensed vEGM matched the atrial pacing artifact morphology template. If the answer to the determination at step 716 is No, then flow goes to back to step 712 (or alternatively back to step 714). During the next instance of step 716, the atrial pacing artifact morphology template is compared to another portion of the sensed vEGM. However, if the answer to the determination at step 716 is Yes, then flow goes to step 722 in FIG. 7A or FIG. 7B, and the portion of the vEGM that is compared to the paced atrial activation morphology template at step 722 in FIG. 7A or 7B (and potentially also to the intrinsic atrial activation morphology template at step 734 in FIG. 7B) is a portion of the vEGM that corresponds to a window following where or when there was a detected match with the atrial pacing artifact morphology template.

There are various different ways in which the vLP, and more specifically a processor and/or a controller thereof, can determine whether there is a match between a portion of the vEGM and one of the stored morphology templates, such as the paced atrial activation morphology template. For example, a morphology of a portion of the vEGM can be compared to the paced atrial activation morphology template to produce a matching score, and these morphologies can be said to match one another when the matching score exceeds a specified threshold. More generally, the morphology of a portion of the vEGM can be compared to the morphology of one or more stored templates, to determine one or more metric indicative of similarity between the compared morphologies. Metrics indicative of similarity are also referred to herein interchangeably as "similarity metrics". Embodiments of the present invention are not limited to use of any specific types of morphology comparison techniques. For example, template matching (also known as pattern matching) or correlation functions can be used. Some template matching or correlation functions align a portion of a signal with a corresponding template and measure the difference in areas under the waveforms. The difference in areas can be a metric indicative of similarity, where the less the difference in areas, the greater the similarity. Alternatively, a percentage match score can be assigned, which is proportional to the difference. Other techniques for comparing waveform morphologies include, but are not limited to, the use of mean square error algorithms and cross correlation or template-matching based finite impulse response (FIR) filters. Other known or future developed morphology comparison techniques can be used. In accordance with certain embodiments, the morphology templates can include characteristics of interest (e.g., related to positive deflection local maximums (peaks), negative deflection local minimums (valleys), and zero crossings) as an amplitude and time relative to a reference time-point.

The length of each cycle of an EGM depends on a patient's heart rate/RR interval. Thus, it may be appropriate to stretch, compress, or adjust (or otherwise normalize) template(s) and/or an obtained EGM signal, before the morphologies of templates and obtained signals are compared to determine their similarity, and more generally, whether a match is detected. It may also be appropriate to normalize the amplitude of a template and/or an obtained EGM signal, prior to a comparison of morphologies.

In accordance with certain embodiments, when the vLP determines that atrial capture failed to occur (responsive to an atrial pacing pulse delivered by the aLP), the vLP can send a message to the aLP to inform the aLP that atrial capture failed and/or to instruct the aLP to increase a voltage of one or more further atrial pacing pulses. This can occur as part of instances of step 742, or following instances of step 742.

In accordance with certain embodiments, when the vLP determines that atrial capture occurred (responsive to an atrial pacing pulse delivered by the aLP), the vLP can send a message to the aLP to inform the aLP that atrial capture succeeded and/or to instruct the aLP to decrease a voltage of one or more further atrial pacing pulses. This can occur as part of instances of step 752, or following instances of step 752. Additionally, or alternatively, after the vLP determines that atrial capture occurred (or failed to occur) responsive to an atrial pacing pulse delivered by the aLP, the vLP can store such information in an atrial capture log which can be periodically uploaded by or to a clinician. Further, if the vLP determines that atrial capture consistently occurs, the vLP may suspend its atrial capture monitoring for at least a period of time, in order to conserve its energy, in an effort to extend the life of its battery (e.g., 114 or 972). Other variations are also possible and within the scope of the embodiments described herein.

As noted above, for one or more of the different types of morphology templates stored in the memory of the vLP there can be at least first and second versions of the morphology template. For example, a first version of a specific type of template (e.g., a paced atrial activation morphology template) can be used when the patient has a first posture (e.g., supine), and the second version of the same specific type of template is to be used when the patient has a second posture (e.g., upright). The high level flow diagram of FIG. 8 is used to summarize how such an embodiment can be implemented.

Figure 8:
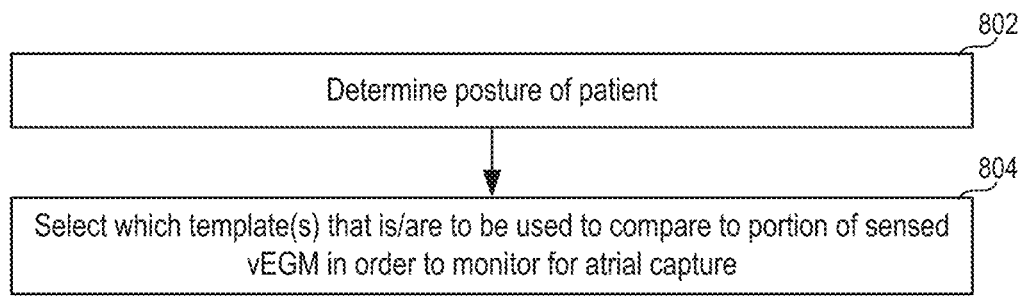
FIG. 8 is a high level flow diagram that is used to explain how the specific template(s) that are used for comparisons, in order to monitor for atrial capture, can be selected based on a posture of the patient.

Referring to FIG. 8, at step 802 the vLP determines a posture of the patient, e.g., using an accelerometer (e.g., 154) and/or some other type of sensor, such as a gyroscope of the vLP. At step 804 the vLP selects which template(s) is/are to be used to compare to a portion of a sensed vLP in order to monitor for atrial capture. For example, the specific template(s) selected at step 804 can be used at one or more of steps 722, 734, and/or 714, described above with reference to FIGS. 7A-7C.

Depending on the availability of reliable beat-by-beat communication between the aLP and the vLP, atrial capture determinations could be achieved in various different manners, which are described below. In certain embodiments, when reliable beat-by-beat communication is available between the aLP and the vLP, the aLP can transmit to the vLP an atrial pace notification message every time an atrial pace stimuli is delivered by the aLP. In such an embodiment, the vLP can monitor the ventricular EGM it obtains for a fixed duration (a "monitor window", e.g., the duration of which is in the range of 150-250 ms) within which the far-field paced atrial activation is expected. When the paced atrial activation template and the running EGM "match" within this "monitor window", then the vLP can confirm atrial capture. Otherwise, the vLP confirms loss of atrial capture and transmits a message to the aLP. Such a message can, e.g., instruct the aLP to increase the atrial pace pulse voltage in the next beat. Such an embodiments provides for closed loop atrial capture management.

When reliable beat-by-beat communication is not available between the aLP and the vLP, the vLP actively monitors for the atrial pacing artifact and following the atrial pacing artifact the vLP searches for a "match" between the paced atrial activation template and the ventricular EGM within the "monitor window" (e.g., the duration of which is in the range of 150-250 ms). If the vLP confirms a match, then the system confirms atrial capture and the vLP starts an AV delay and schedules a ventricular pace to maintain AV synchrony. If the vLP does not identify a "match" within the "monitor window", the vLP recognizes a loss of atrial capture. The vLP can save information related to the loss of capture as an alert and prepare to send it to either a remote monitoring device or notify the aLP of the loss of capture when communication between the aLP and the vLP is established again. In the meantime, the vLP could either search for an intrinsic atrial activation beat based on a saved intrinsic atrial activation template and deliver synchronized ventricular pace (i.e. VDD mode) or enter VVI mode depending on the setting of the vLP.

More generally, the vLP can monitor communication quality between the aLP and the vLP, and the based on the communication quality can determine how to monitor for atrial capture. For example, the vLP (or more specifically a processor and/or controller thereof) can monitor a communication quality between the aLP and the vLP and compare the communication quality to a specified threshold. When the communication quality is above the specified threshold, the vLP actively monitors for an atrial pace notification message sent by the aLP, and the portion of the sensed vEGM that the vLP compares to the paced atrial activation morphology template (in order to determine whether a match therebetween is detected) is a portion of the sensed vEGM within a specified window following when (or where) the vLP receives an atrial pace notification message from the aLP. When the communication quality is below the specified threshold, the vLP actively monitors for an atrial pacing artifact using the atrial pacing artifact morphology template, and the portion of the sensed vEGM that the vLP compares to the paced atrial activation morphology template (in order to determine whether a match therebetween is detected) is a portion of the sensed vEGM within a specified window following when or where the vLP detects an atrial pacing artifact.

The communication quality that is monitored by the vLP can be indicative of a quality of one or more messages and/or a quality of the channel over which one or more messages are received by the vLP from the aLP. There are various different ways in which the vLP can monitor such communication quality. The vLP can perform error detection and correction on one or more messages received from the aLP and determine the communication quality based on results of the error detection and correction. Additionally, or alternatively, the vLP can measure an amplitude and/or power of a received signal including one or more messages received from the aLP and determine the communication quality based on results of measuring the amplitude and/or power. Additionally, or alternatively, the vLP can measure noise associated with a channel over which messages are received from the aLP and determine the communication quality based on results of measuring noise. Additionally, or alternatively, the vLP can measure time intervals between one or more consecutive messages received from the aLP and determine the communication quality based on the measured time intervals. In normal operation, the aLP should send messages to vLP each time an atrial sense or pace event occurs, which means the time interval between two consecutive messages from the aLP should not be greater than a physiological or programmed length plus a margin (e.g. 1500 ms). The vLP can measure the time interval between consecutive messages (atrial pace or sense) received from the aLP and determine that the communication is "interrupted" if any single time interval exceeds a long communication gap threshold (e.g. 3 seconds) or there were frequent short communication gaps (e.g. at least 4 inter-message intervals exceed 1.5 seconds within one minute). These are just a few examples of how the vLP can monitor communication quality, which examples are not intended to be all inclusive. Other variations are also possible and within the scope of the embodiments described herein.

Figure 9:
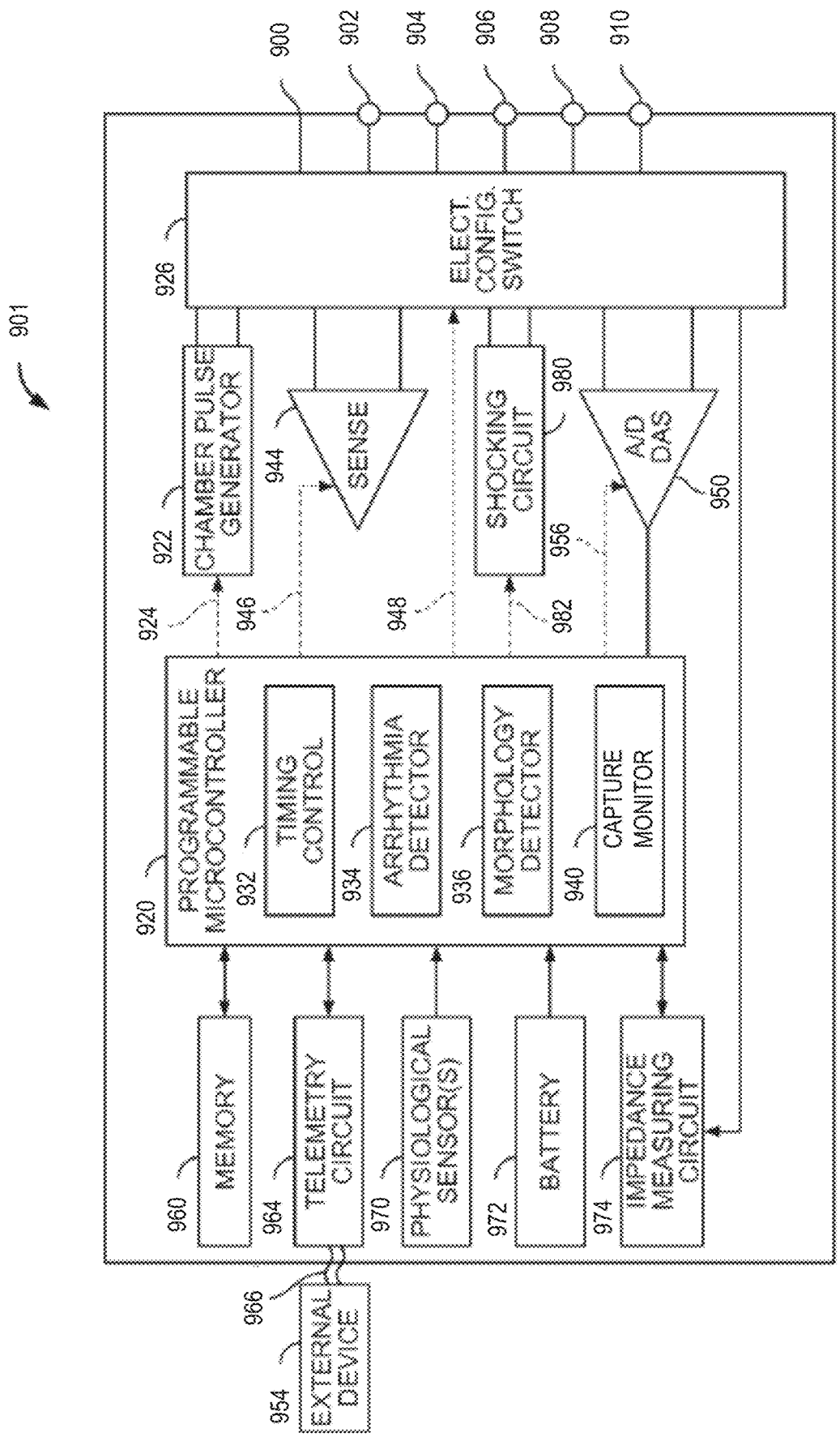
FIG. 9 shows a block diagram of one embodiment of an LP that is implanted into a patient as part of an implantable cardiac system in accordance with certain embodiments herein.

FIG. 9 shows a block diagram of one embodiment of an LP 901 that is implanted into the patient as part of the implantable cardiac system in accordance with certain embodiments herein. The LP 901 may be implemented as a full-function biventricular pacemaker, equipped with both atrial and ventricular sensing and pacing circuitry for four chamber sensing and stimulation therapy (including both pacing and shock treatment). Optionally, the LP 901 may provide full-function cardiac resynchronization therapy. Alternatively, the LP 901 may be implemented with a reduced set of functions and components. For instance, the IMD may be implemented without ventricular sensing and pacing. The LP 901 can be the LP 102 or 104.

The LP 901 has a housing 900 to hold the electronic/computing components. The housing 900 (which is often referred to as the "can", "case", "encasing", or "case electrode") may be programmably selected to act as the return electrode for certain stimulus modes. The housing 900 may further include a connector (not shown) with a plurality of terminals 902, 904, 906, 908, and 910. The terminals may be connected to electrodes that are located in various locations on the housing 900 or elsewhere within and about the heart. the LP 901 includes a programmable microcontroller 920 that controls various operations of the LP 901, including cardiac monitoring and stimulation therapy. The microcontroller 920 includes a microprocessor (or equivalent control circuitry), RAM and/or ROM memory, logic and timing circuitry, state machine circuitry, and I/O circuitry.

The LP 901 further includes a pulse generator 922 that generates stimulation pulses and communication pulses for delivery by one or more electrodes coupled thereto. The pulse generator 922 is controlled by the microcontroller 920 via a control signal 924. The pulse generator 922 may be coupled to the select electrode(s) via an electrode configuration switch 926, which includes multiple switches for connecting the desired electrodes to the appropriate I/O circuits, thereby facilitating electrode programmability. The switch 926 is controlled by a control signal 928 from the microcontroller 920.

In the embodiment of FIG. 9, a single pulse generator 922 is illustrated. Optionally, the IMD may include multiple pulse generators, similar to the pulse generator 922, where each pulse generator is coupled to one or more electrodes and controlled by the microcontroller 920 to deliver select stimulus pulse(s) to the corresponding one or more electrodes.

The microcontroller 920 is illustrated as including timing control circuitry 932 to control the timing of the stimulation pulses (e.g., pacing rate, atrio-ventricular (AV) delay, atrial interconduction (A-A) delay, or ventricular interconduction (V-V) delay, etc.). Timing control circuitry 932 may also be used for the timing of refractory periods, blanking intervals, noise detection windows, evoked response windows, alert intervals, marker channel timing, and so on. The microcontroller 920 also has an arrhythmia detector 934 for detecting arrhythmia conditions and a morphology detector 936. Although not shown, the microcontroller 920 may further include other dedicated circuitry and/or firmware/software components that assist in monitoring various conditions of the patient's heart and managing pacing therapies. The microcontroller can include a processor. The microcontroller, and/or the processor thereof, can be used to perform the methods of the present technology described herein.

The microcontroller 920 is also shown as including a capture monitor 940, which can be used to monitor for atrial capture, using embodiments of the present technology described above, e.g., with reference to FIGS. 5-8. The capture monitor 940 can more generally be implemented using hardware, software, firmware, and/or combinations thereof. The microcontroller can include a processor. The microcontroller, and/or the processor thereof, can be used to perform the methods of the present technology described herein.

The LP 901 can be further equipped with a communication modem (modulator/demodulator) to enable wireless communication with the remote slave pacing unit. Such a modem may include one or more transmitters and two or more receivers as discussed herein in connection with FIG. 1B. In one implementation, the modem may use low or high frequency modulation. As one example, the modem may transmit i2i messages and other signals through conductive communication between a pair of electrodes. Such a modem may be implemented in hardware as part of microcontroller 920, or as software/firmware instructions programmed into and executed by microcontroller 920. Alternatively, the modem may reside separately from the microcontroller as a standalone component.

The LP 901 includes a sensing circuit 944 selectively coupled to one or more electrodes, that perform sensing operations, through the switch 926 to detect the presence of cardiac activity in the right chambers of the heart. The sensing circuit 944 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. The switch 926 determines the sensing polarity of the cardiac signal by selectively closing the appropriate switches. In this way, the clinician may program the sensing polarity independent of the stimulation polarity.

The output of the sensing circuit 944 is connected to the microcontroller 920 which, in turn, triggers or inhibits the pulse generator 922 in response to the presence or absence of cardiac activity. The sensing circuit 944 receives a control signal 946 from the microcontroller 920 for purposes of controlling the gain, threshold, polarization charge removal circuitry (not shown), and the timing of any blocking circuitry (not shown) coupled to the inputs of the sensing circuitry.

In the embodiment of FIG. 9, a single sensing circuit 944 is illustrated. Optionally, the IMD may include multiple sensing circuits, similar to the sensing circuit 944, where each sensing circuit is coupled to one or more electrodes and controlled by the microcontroller 920 to sense electrical activity detected at the corresponding one or more electrodes. The sensing circuit 944 may operate in a unipolar sensing configuration or in a bipolar sensing configuration.

The LP 901 further includes an analog-to-digital (ND) data acquisition system (DAS) 950 coupled to one or more electrodes via the switch 926 to sample cardiac signals across any pair of desired electrodes. Data acquisition system 950 is configured to acquire intracardiac electrogram signals, convert the raw analog data into digital data, and store the digital data for later processing and/or telemetric transmission to an external device 954 (e.g., a programmer, local transceiver, or a diagnostic system analyzer). The data acquisition system 950 is controlled by a control signal 956 from the microcontroller 920.

The microcontroller 920 is coupled to a memory 960 by a suitable data/address bus. The programmable operating parameters used by the microcontroller 920 are stored in the memory 960 and used to customize the operation of the LP 901 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy. The memory 960 can also be used to store the various templates described above.

The operating parameters of the LP 901 may be non-invasively programmed into the memory 960 through a telemetry circuit 964 in telemetric communication via a communication link 966 with an external device 954. The telemetry circuit 964 allows intracardiac electrograms and status information relating to the operation of the LP 901 (as contained in microcontroller 920 or memory 960) to be sent to the external device 954 through the communication link 966.

The LP 901 can further include magnet detection circuitry (not shown), coupled to the microcontroller 920, to detect when a magnet is placed over the unit. A magnet may be used by a clinician to perform various test functions of the LP 901 and/or to signal the microcontroller 920 that the external device 954 is in place to receive or transmit data to the microcontroller 920 through the telemetry circuits 964.

The LP 901 can further include one or more physiological sensors 970. Such sensors are commonly referred to as "rate-responsive" sensors because they are typically used to adjust pacing stimulation rates according to the exercise state of the patient. However, the physiological sensor 970 may further be used to detect changes in cardiac output, changes in the physiological condition of the heart, or diurnal changes in activity (e.g., detecting sleep and wake states). Signals generated by the physiological sensors 970 are passed to the microcontroller 920 for analysis. The microcontroller 920 responds by adjusting the various pacing parameters (such as rate, AV Delay, V-V Delay, etc.) at which the atrial and ventricular pacing pulses are administered. While shown as being included within the LP 901, the physiological sensor(s) 970 may be external to the LP 901, yet still be implanted within or carried by the patient. Examples of physiologic sensors might include sensors that, for example, sense respiration rate, pH of blood, ventricular gradient, activity, position/posture, minute ventilation (MV), and so forth.

A battery 972 provides operating power to all of the components in LP 901. The battery 972 is preferably capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 972 also desirably has a predictable discharge characteristic so that elective replacement time can be detected. As one example, the LP 901 employs lithium/silver vanadium oxide batteries.

The LP 901 further includes an impedance measuring circuit 974, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. The impedance measuring circuit 974 is coupled to switch 926 so that any desired electrode may be used. In this embodiment the LP 901 further includes a shocking circuit 980 coupled to the microcontroller 920 by a data/address bus 982. However, the LP need not include a shocking circuit.

In some embodiments, the LPs 102 and 104 are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

In the embodiments described above, e.g., with reference to FIGS. 7A-7C, a vLP is used to monitor for atrial capture responsive to an atrial pacing pulse delivered by an aLP. Similar techniques to those described above can be used by an aLP to monitor for ventricular capture responsive to a ventricular pacing pulsed delivered by a vLP. More specifically, an aLP can similarly store one or more morphology templates that can be used by the aLP to monitor for ventricular capture based on an aLP. Such templates can include, e.g., a paced ventricular activation morphology template, an intrinsic ventricular activation morphology template, and a ventricular pacing artifact morphology template, and multiple versions of each type can be stored such that appropriate templates can be selected for comparisons to an aEGM depending on the specific posture of the patient. Further details of such ventricular capture monitoring embodiments can be appreciated from the above discussion of the atrial capture monitoring embodiments, and thus need not be repeated.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 7A, 7B and 7C. For another example, it is possible to change the boundaries of some of the blocks shown in FIGS. 1B and 9.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

What is claimed is:

1. An implantable system, comprising:
   an atrial leadless pacemaker (aLP) including
      a pulse generator configured to produce atrial pacing pulses; and
      at least two electrodes electrically coupled to the pulse generator and configured to deliver the atrial pacing pulses produced by the pulse generator to a patient's atrium;
   a ventricular leadless pacemaker (vLP) including
      at least two electrodes;
      a sensing circuit electrically coupled to the at least two electrodes of the vLP and configured to sense a ventricular electrogram (vEGM);
      a memory that stores one or more morphology templates including a paced atrial activation morphology template corresponding to far-field atrial signal components expected to be present in the vEGM when one of the atrial pacing pulses delivered by the aLP captures atrial tissue;
      at least one of a processor or a controller configured to
         compare a morphology of a portion of the sensed vEGM to the paced atrial activation morphology template to thereby determine whether a match therebetween is detected;
         determine that atrial capture occurred responsive to the one of the atrial pacing pulses delivered by the aLP, based on a match being detected between the morphology of the portion of the sensed vEGM and the paced atrial activation morphology template; and
         determine that atrial capture failed to occur responsive to the one of the atrial pacing pulses delivered by the aLP, based on a match failing to be detected between the morphology of the portion of the sensed vEGM and the paced atrial activation morphology template.

2. The system of claim 1, wherein the one or more morphology templates stored in the memory of the vLP also includes an intrinsic atrial activation morphology template corresponding to further far-field atrial signal components expected to be present in the vEGM sensed by the vLP when an intrinsic atrial activation occurs, and wherein the at least one of the processor or the controller of the vLP is configured to:
   compare the morphology of the portion of the sensed vEGM, that is compared to the paced atrial activation morphology template, to the intrinsic atrial activation morphology template to determine whether a match therebetween is detected; and
   determine whether the atrial capture occurred or failed to occur responsive to the one of the atrial pacing pulses delivered by the aLP, also based on whether the vLP detects a match between the morphology of the portion of the sensed vEGM and the intrinsic atrial activation morphology template.

3. The system of claim 1, wherein the one or more morphology templates stored in the memory of the vLP also includes an atrial pacing artifact morphology template corresponding to further far-field atrial signal components expected to be present in the vEGM sensed by the vLP when the one of the atrial pacing pulses is delivered by the aLP, and wherein the at least one of the processor or the controller of the vLP is configured to:
   compare a morphology of a further portion of the sensed vEGM to the atrial pacing artifact morphology template to thereby determine whether a match therebetween is detected; and
   detect an atrial pacing artifact when the vLP detects a match between the morphology of the further portion of the sensed vEGM and the atrial pacing artifact morphology template;
   wherein the portion of the sensed vEGM that is compared to the paced atrial activation morphology template, in order to determine whether a match therebetween is detected, corresponds to a specified window following where or when the atrial pacing artifact is detected.

4. The system of claim 2, wherein:
   for a type of morphology template, of the one or more morphology templates stored in the memory of the vLP, there are at least first and second versions of the type of morphology template, wherein the first version is to be used when the patient has a first posture, and the second version is to be used when the patient has a second posture;
   the vLP comprises a sensor that can be used to monitor a posture of a patient within which the vLP and the aLP is implanted; and
   the at least one of the processor or the controller of the vLP is configured to monitor the posture of the patient using the sensor; and
   select, based on the monitored posture of the patient, which version of of the type of morphology template is templates is to be compared to the morphology of the portion of the sensed vEGM to thereby determine whether a match therebetween is detected.

5. A leadless pacemaker (LP) comprising:
   at least two electrodes;
   a sensing circuit electrically coupled to the at least two electrodes and configured to sense an electrogram (EGM);
   a memory that stores one or more morphology templates including a first morphology template corresponding to far-field signal components expected to be present in the EGM when a pacing pulse delivered to a remote cardiac chamber by a further LP captures tissue of the remote cardiac chamber;
   at least one of a processor or a controller configured to
      compare a morphology of a portion of the sensed EGM to the first morphology template to thereby determine whether a match therebetween is detected;
      determine that capture of the remote cardiac chamber occurred responsive to the pacing pulse delivered by the further LP, based on a match being detected between the morphology of the portion of the sensed EGM and the first morphology template; and
      determine that capture of the remote cardiac chamber failed to occur responsive to the pacing pulse delivered by the further LP, based on a match failing to be detected between the morphology of the portion of the sensed EGM and the first morphology template.

6. The LP of claim 5, wherein the one or more morphology templates stored in the memory of the LP also includes a second morphology template corresponding to second far-field signal components expected to be present in the EGM sensed by the LP when an intrinsic activation of the remote chamber occurs, and wherein the at least one of the processor or the controller of the LP is configured to:
compare the morphology of the portion of the sensed EGM, that is compared to the first morphology template, to the second morphology template to determine whether a match therebetween is detected; and
determine whether capture of the remote chamber occurred or failed to occur responsive to the pacing pulse delivered by the further LP, also based on whether the LP detects a match between the morphology of the portion of the sensed EGM and the second morphology template.

7. The LP of claim 5, wherein the one or more morphology templates stored in the memory of the LP also includes a second morphology template corresponding to second far-field signal components expected to be present in the EGM sensed by the LP when the pacing pulse is delivered by the further LP to the remote chamber, and wherein the at least one of the processor or the controller of the LP is configured to:
compare a morphology of a further portion of the sensed EGM to the second morphology template to thereby determine whether a match therebetween is detected; and
detect a pacing artifact from the remote chamber when the LP detects a match between the morphology of the further portion of the sensed vEGM and the second morphology template;
wherein the portion of the sensed EGM that is compared to the first morphology template, in order to determine whether a match therebetween is detected, corresponds to a specified window following where or when the atrial pacing artifact is detected.

8. The LP of claim 7, wherein the LP is configured to receive messages from the further LP, and the at least one of the processor or the controller of the LP is configured to:
monitor communication quality between the further LP and the LP;
when the communication quality is above a specified threshold, monitor for a pace notification message sent by the further LP, and the portion of the sensed EGM that is compared to the first morphology template, in order to determine whether a match therebetween is detected, corresponds to a specified window following when or where the LP receives the pace notification message from the further LP; and
when the communication quality is below the specified threshold, monitor for the pacing artifact using the second morphology template, and the portion of the sensed EGM that is compared to the first morphology template, in order to determine whether a match therebetween is detected, corresponds to a further specified window following when or where the LP detects the pacing artifact.

9. The LP of claim 5, wherein:
for a type of morphology template, of the one or more morphology templates stored in the memory of the LP, there are at least two versions of the type of morphology template;

the LP comprises a sensor that can be used to monitor a posture of a patient within which the LP and the further LP are implanted; and
the at least one of the processor or the controller of the LP is configured to monitor a posture of the patient using the sensor; and
select, based on the monitored posture of the patient, which version of the type of morphology template stored in the memory is to be compared to the morphology of the portion of the sensed EGM to thereby determine whether a match therebetween is detected.

10. For use within an implantable system including an atrial leadless pacemaker (aLP) and a ventricular leadless pacemaker (vLP), a method comprising:
storing within a memory of the vLP one or more morphology templates including a paced atrial activation morphology template corresponding to far-field atrial signal components expected to be present in a ventricular electrogram (vEGM) sensed by the vLP when an atrial pacing pulse delivered by the aLP captures atrial tissue;
the vLP sensing the vEGM using at least two electrodes of the vLP;
the vLP comparing a morphology of a portion of the sensed vEGM to the paced atrial activation morphology template to thereby determine whether a match therebetween is detected; and
the vLP determining whether atrial capture occurred or failed to occur responsive to the atrial pacing pulse delivered by the aLP, based on whether the vLP detects a match between the morphology of the portion of the sensed vEGM and the paced atrial activation morphology template.

11. The method of claim 10, wherein:
the one or more morphology templates stored in the memory of the vLP includes at least first and second paced atrial activation morphology templates;
the first atrial activation morphology template corresponds to first far-field atrial signal components expected to be present in the vEGM sensed by the vLP when the atrial pacing pulse delivered by the aLP captures atrial tissue and a patient has a first posture;
the second atrial activation morphology template corresponds to second far-field atrial signal components expected to be present in the vEGM sensed by the vLP when the atrial pacing pulse delivered by the aLP captures atrial tissue and the patient has a second posture;
the method further comprising:
the vLP monitoring a posture of the patient using a sensor of the vLP; and
selecting, based on the posture of the patient, one of the first and the second paced atrial activation morphology templates to compare to the portion of the sensed vEGM to thereby determine whether a match therebetween is detected.

12. The method of claim 10, wherein the one or more morphology templates stored in the memory of the vLP also includes an intrinsic atrial activation morphology template corresponding to further far-field atrial signal components expected to be present in the vEGM sensed by the vLP when an intrinsic atrial activation occurs, and the method further comprising:
the vLP also comparing the morphology of the portion of the sensed vEGM, that is compared to the paced atrial activation morphology template, to the intrinsic atrial activation morphology template to determine whether a match therebetween is detected; and wherein the vLP determining whether the atrial capture occurred or failed to occur responsive to the atrial pacing pulse delivered by the aLP, is also based on whether the vLP detects a match between the morphology of the portion of the sensed vEGM and the intrinsic atrial activation morphology template.

13. The method of claim 12, wherein for a type of morphology template, of the one or more morphology templates stored in the memory of the vLP, there are at least first and second versions of the type of morphology template, wherein the first version is to be used when a patient has a first posture, and the second version is to be used when the patient has a second posture, and wherein the method further comprises monitoring a posture of the patient and selecting which version of the type of morphology template is to be compared to the morphology of the portion of the sensed vEGM to thereby determine whether a match therebetween is detected.

14. The method of claim 10, wherein the one or more morphology templates stored in the memory of the vLP also includes an atrial pacing artifact morphology template corresponding to further far-field atrial signal components expected to be present in the vEGM sensed by the vLP when the atrial pacing pulse is delivered by the aLP, and the method further comprising:

the vLP comparing a morphology of a further portion of the sensed vEGM to the atrial pacing artifact morphology template to thereby determine whether a match therebetween is detected; and the vLP detecting an atrial pacing artifact when the vLP detects a match between the morphology of the further portion of the sensed vEGM and the atrial pacing artifact morphology template;

wherein the vLP comparing the morphology of the portion of the sensed vEGM to the paced atrial activation morphology template to thereby determine whether a match therebetween is detected, is performed by the vLP in response to the vLP detecting a match between the morphology of the further portion of the sensed vEGM and the atrial pacing artifact morphology template; and wherein the portion of the sensed vEGM that the vLP compares to the paced atrial activation morphology template, in order to determine whether a match therebetween is detected, corresponds to a specified window following where or when the atrial pacing artifact is detected.

15. The method of claim 10, wherein the aLP and the vLP are configured to communicate with one another, and wherein the aLP is configured to send an atrial pace notification message to the vLP prior to the aLP delivering the atrial pacing pulse to an atrium, and the method further comprising:

the vLP receiving the atrial pace notification message from the aLP;

wherein the vLP comparing the morphology of the portion of the sensed vEGM to the paced atrial activation morphology template to thereby determine whether a match therebetween is detected, is performed by the vLP in response to the vLP receiving the atrial pace notification message from the aLP; and wherein the portion of the sensed vEGM that the vLP compares to the paced atrial activation morphology template, in order to determine whether a match therebetween is detected, corresponds to a specified window following when or where the vLP receives the atrial pace notification message from the aLP.

16. The method of claim 10, wherein:

the aLP and the vLP are capable of communicating with one another by sending messages from one to the other;

the aLP is configured to send an atrial pace notification message to the vLP prior to the aLP delivering the atrial pacing pulse to an atrium;

the one or more morphology templates stored in the memory of the vLP also includes an atrial pacing artifact morphology template corresponding to further far-field atrial signal components expected to be present in the vEGM sensed by the vLP when the atrial pacing pulse is delivered by the aLP; and the method further comprising the vLP monitoring communication quality between the aLP and the vLP;

when the communication quality is above a specified threshold, the vLP monitors for the atrial pace notification message sent by the aLP, and the portion of the sensed vEGM that the vLP compares to the paced atrial activation morphology template, in order to determine whether a match therebetween is detected, corresponds to a specified window following when or where the vLP receives the atrial pace notification message from the aLP; and when the communication quality is below the specified threshold, the vLP monitors for an atrial pacing artifact using the atrial pacing artifact morphology template, and the portion of the sensed vEGM that the vLP compares to the paced atrial activation morphology template, in order to determine whether a match therebetween is detected, corresponds to a further specified window following when or where the vLP detects the atrial pacing artifact.

17. The method of claim 16, wherein the vLP monitoring the communication quality between the aLP and the vLP comprises at least one of the following:

the vLP performing error detection and correction on one or more messages received from the aLP and determining the communication quality based on results of the error detection and correction;

the vLP measuring an amplitude or power of a received signal including the one or more messages received from the aLP and determining the communication quality based on results of the measuring the amplitude or power;

the vLP measuring noise associated with a channel over which the one or more messages are received from the aLP and determining the communication quality based on results of the measuring noise; or the vLP measuring time intervals between one or more consecutive messages received from the aLP and determining the communication quality based on the measured time intervals;

wherein the communication quality is indicative of at least one of a quality of the one or more messages or a quality of the channel over which the one or more messages are received by the vLP from the aLP.

18. The method of claim 10, further comprising:

after the vLP determines that the atrial capture failed to occur responsive to the atrial pacing pulse delivered by the aLP, the vLP sending a message to the aLP to inform the aLP that the atrial capture failed or to instruct the aLP to increase a voltage of one or more further atrial pacing pulses.

19. The method of claim 10, further comprising:

after the vLP determines that the atrial capture occurred responsive to the atrial pacing pulse delivered by the aLP, the vLP sending a message to the aLP to inform the aLP that the atrial capture succeeded or to instruct the aLP to decrease a voltage of one or more further atrial pacing pulses.

20. The method of claim 10, further comprising:

after a match is detected between a said morphology template stored in the memory of the vLP and the portion of the sensed vEGM, using the portion of the sensed vEGM that matched the said morphology template to update the said morphology template stored in the memory.

* * * * *